US009791267B2

(12) United States Patent
Bismuth et al.

(10) Patent No.: US 9,791,267 B2
(45) Date of Patent: Oct. 17, 2017

(54) DETERMINING THREE-DIMENSIONAL INFORMATION FROM PROJECTIONS OR PLACEMENT OF TWO-DIMENSIONAL PATTERNS

(71) Applicant: Bourbaki 13, Inc., Seattle, WA (US)

(72) Inventors: Robert Bismuth, Seattle, WA (US); William D. Orner, Mountain View, CA (US); Jacob Rapoport, Seattle, WA (US); Amit Rohatgi, Los Altos, CA (US)

(*) Notice: Subject to any disclaimer, the term of this patent is extended or adjusted under 35 U.S.C. 154(b) by 186 days.

(21) Appl. No.: 14/442,707

(22) PCT Filed: May 12, 2015

(86) PCT No.: PCT/US2015/030432
§ 371 (c)(1),
(2) Date: May 13, 2015

(87) PCT Pub. No.: WO2015/183550
PCT Pub. Date: Dec. 3, 2015

(65) Prior Publication Data
US 2016/0252346 A1    Sep. 1, 2016

Related U.S. Application Data

(60) Provisional application No. 61/992,446, filed on May 27, 2014, provisional application No. 62/104,559, filed on Jan. 16, 2015.

(51) Int. Cl.
*G01B 11/25* (2006.01)
*A61B 5/107* (2006.01)
(Continued)

(52) U.S. Cl.
CPC .......... *G01B 11/254* (2013.01); *A61B 5/1075* (2013.01); *A61B 5/1077* (2013.01);
(Continued)

(58) Field of Classification Search
CPC ....... G01B 11/14; G01B 11/22; G01B 11/002; G01B 11/2513; G01B 11/2518; G06K 9/2036
(Continued)

(56) References Cited

U.S. PATENT DOCUMENTS 4,647,208 A    3/1987 Bieman
6,549,289 B1   4/2003 Ellis
(Continued)

OTHER PUBLICATIONS

International Search Report and Written Opinion of International Application No. PCT/US2015/030432; Date of Mailing: Aug. 21, 2015; 13 pages.
(Continued)

*Primary Examiner* — Hoa Pham
(74) *Attorney, Agent, or Firm* — Lane Powell, P.C.

(57) ABSTRACT

Embodiments of a shape measurement system and related methods are disclosed. In some embodiments, the system places a two-dimensional initial pattern, which can be implemented as a standalone molding or can be attached to a light source or printed on an outfit, onto a surface of a three-dimensional object. The system captures a transformed version of the initial pattern in two dimensions that is distorted due to the varying depth of the surface. The system then analyzes the transformed pattern and derives three-dimensional information regarding the target object. The analysis, which can incorporate a calibration process, can rely on the projection nature of the light source, the isomorphism/non-isomorphism of the initial pattern, and other factors.

15 Claims, 25 Drawing Sheets

(51) Int. Cl.
*G06T 7/00* (2017.01)
*A41H 1/02* (2006.01)
*A61B 5/00* (2006.01)
*A41H 3/04* (2006.01)

(52) U.S. Cl.
CPC ........ *A61B 5/1079* (2013.01); *G01B 11/2513* (2013.01); *G06T 7/0057* (2013.01); *G06T 7/0065* (2013.01); *A41H 1/02* (2013.01); *A41H 3/04* (2013.01); *A61B 5/6898* (2013.01); *A61B 2503/40* (2013.01)

(58) Field of Classification Search
USPC .................................. 356/601–623; 382/154
See application file for complete search history.

(56) References Cited

U.S. PATENT DOCUMENTS

| | | | |
|---|---|---|---|
| 9,311,715 B2* | 4/2016 | Rafii | G06K 9/00201 |
| 2002/0057832 A1 | 5/2002 | Proesmans et al. | |
| 2006/0192978 A1 | 8/2006 | Laguarta Bertran et al. | |
| 2009/0097039 A1* | 4/2009 | Kawasaki | G01B 11/2509 356/603 |
| 2010/0074532 A1* | 3/2010 | Gordon | G01B 11/25 382/203 |
| 2011/0216948 A1* | 9/2011 | Yalla | G06K 9/00006 382/125 |
| 2012/0105868 A1* | 5/2012 | Nomura | G01B 11/25 356/610 |
| 2013/0296711 A1 | 11/2013 | Curiel et al. | |
| 2015/0221093 A1* | 8/2015 | Sagawa | G06T 7/0057 345/419 |

OTHER PUBLICATIONS

Pavlidis, T. "Algorithms for Graphics and Image Processing," S.I., Computer Science Press, Springer 2012, pp. 142-148.

* cited by examiner $$Z = \text{depth of object} = f \begin{cases} Area = f(m_{00}) \\ Centroid = f(m_{01}, m_{10}, m_{00}) \\ Bounding\ box = \{\min, \max\}\{x, y\ of\ contour\} \\ \qquad\qquad\quad = B \\ Convex\ hull = |B - C|, \text{ where B=Bounding Box, C=Contour} \\ Curvature = stretch \text{ (parametrized and controlled)} \end{cases}$$

*FIG. 23*

# DETERMINING THREE-DIMENSIONAL INFORMATION FROM PROJECTIONS OR PLACEMENT OF TWO-DIMENSIONAL PATTERNS

PRIORITY CLAIM

The present application is a United States national phase application filed pursuant to 35 USC §371 of International Patent Application Serial No. PCT/US2015/030432, entitled DETERMINING THREE-DIMENSIONAL INFORMATION FROM PROJECTIONS OR PLACEMENT OF TWO-DIMENSIONAL PATTERNS, filed May 12, 2015; which application claims priority to and benefit from U.S. Provisional Patent Applications 61/992,446, filed May 27, 2014 and titled "METHOD FOR VISUAL SIZING OF HUMAN ANATOMY", and 62/104,559, filed Jan. 16, 2015 and titled "DETERMINING THREE-DIMENSIONAL INFORMATION FROM PROJECTIONS OR PLACEMENT OF TWO-DIMENSIONAL PATTERNS". The entire content of the provisional applications is herein expressly incorporated by reference.

TECHNICAL FIELD

The present application is generally related to determining three-dimensional information of an object from projections or placement of two-dimensional patterns onto the object.

BACKGROUND

Often times, it is necessary to have the measurements of an object. The object can be a part of a person's body, which has a varied, irregular shape, and the measurements would be used to fit that part into a wearable piece. For example, the object can be the person's feet, and the wearable piece can be a pair of shoes. The object can also be inanimate, large or heavy, and the measurements would be used when the object needs to be covered, transported, valuated, etc. As one example, the object can be the trunk of a tree, and the measurements can be used to decide whether to cut the tree down and how to transport the resulting log. As another example, the object can be a large gold statute, and the measurements can be used to determine how much it is worth.

For parts of the human body, for example, the irregular shape presents a challenge in obtaining good measurements. In addition, the shape of the human body can fluctuate over time, adding to the complexity of the challenge. On the other hand, when an object is inanimate, large, or heavy, it can be difficult to take the measurements overall. It would be useful to be able to easily obtain good measurements.

BRIEF DESCRIPTION OF THE DRAWINGS

Various embodiments are disclosed in the following detailed description and accompanying drawings.

FIG. 23 illustrates how the depth of a point on the target object can be computed from various features of the projected pattern.

DETAILED DESCRIPTION

This application discloses a shape measurement system that allows a user to easily take measurements of a target object. The system projects or places two-dimensional initial patterns onto the target object and calculates three-dimensional information regarding the target object based on the two-dimensional projected patterns, which are transformed from the initial patterns due to the varying depths of the projection surface. The system typically requires the user to merely gain access to a camera, which can be embedded into a mobile device, and optionally a light source, and the system quickly produces accurate and comprehensive measurements of the target object.

The shape measurement system has many potential applications. In the fashion industry, the system can facilitate the fitting process and help reduce shipping efforts. In the medical devices industry, the system can assist in the making of prostheses, casts, braces, and biometric devices. In the exercise and fitness industry, the system provides monitoring capabilities for weight loss and body sculpting efforts and can help with the manufacturing of fitness apparel and equipment, such as a helmet or shoes and boots. In the animal care industry, the system can similarly facilitate the fitting of an animal into an outfit or a gear. In the motion capture industry, the system enables the tracking of body movement and positioning, such as for animation purposes. In the printing industry, the system makes it easy to replicate an existing object with three-dimensional printing. In the furniture industry, the system similarly makes it easy to model new furniture for individual custom fit, model furniture after existing pieces and to replace parts or produce covers for existing pieces. In the car and airplane industry, the system enables and a structure analysis showing the relationships among different parts of the vehicle as well as a fitness analysis between the interior of the vehicle and a customer driving the vehicle.

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and the equivalent.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Figure 1:
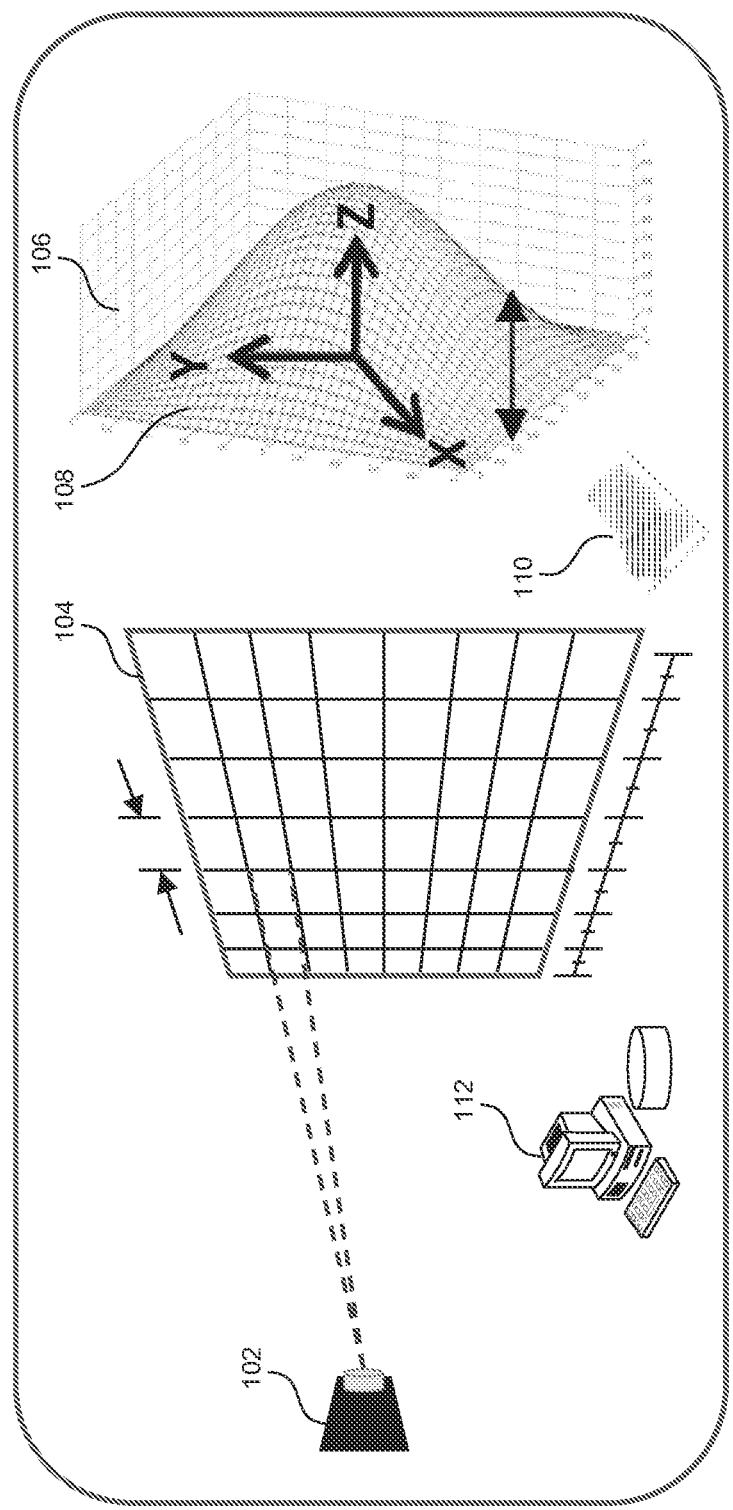
FIG. 1 illustrates an example setup of a shape measurement system disclosed in the present application.

FIG. 1 illustrates an example setup of the shape measurement system disclosed in the present application. In some embodiments, the system includes a light source 102 and a pattern molding 104 embedding a two-dimensional initial pattern. The light source 102, the pattern molding 104, and a target object 106 regarding which three-dimensional information is to be obtained are positioned such that the two-dimensional pattern is projected onto a surface of the target object 106 resulting in a distorted pattern 108. The system also includes a camera 1 10, which then captures the distorted pattern 108 in two dimensions. Furthermore, the system includes a processor and memory 1 12, which manages the different components of the system and performs computations, including analyzing the distorted pattern 108 to determine how the surface moves up and down and derives three-dimensional information regarding the target object. The analysis can take into consideration the characteristics of the initial pattern, the relative placement of the light source 102, the pattern molding 104, the target object 106, the camera 1 10, or other factors. In addition, the system can include a display screen and an input device for communication with a user of the system.

In some embodiments, the camera 1 10, the processor and memory 1 12, and the display screen are all combined in a single device, such as a cellular phone, a tablet, a desktop computer, a laptop computer, or a wearable device. Alternatively, the processor and memory 1 12 are located separately from the rest of the system. In this case, the processor and memory 1 12 communicate with the rest of the system, specifically the camera 1 10 or the display screen, across any type of network known to someone of ordinary skill in the art, such as a cellular network or the Internet.

In some embodiments, the initial pattern can be projected onto multiple surfaces of the target object by rotating the target object or the components of the system around the target object. In addition, multiple initial patterns can be used for the same surface or different surfaces of the target object. In either case, the processor coupled with the memory can synthesize information obtained from multiple distorted patterns in deriving the three-dimensional information regarding the target object 106.

By virtue of such a setup, the shape management system can obtain three-dimensional information of a target object based on projections or placement of two-dimensional patterns onto the target object. The system achieves this goal without making direct contact with the target object and without requiring substantial movement of the target object. These features can be useful when the target object is difficult to move or measure. They also provide the convenience of obtaining shape measurements at a chosen location and without having to interact with other persons or objects.

Figure 2:
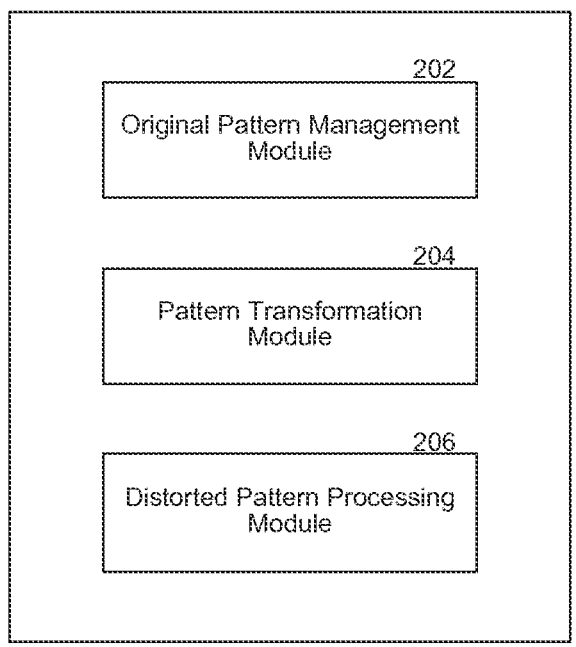
FIG. 2 illustrates example components of the computing portion of the shape measurement system, comprising one or more processors or memories.

FIG. 2 illustrates example components of the computing portion of the shape measurement system, comprising one or more processors or memories. In some embodiments, the computing portion includes an original pattern management module 202, a pattern transformation module 204, and a distorted pattern processing module 206.

In some embodiments, the original pattern management module 202 manages the creation and selection of two-dimensional initial patterns to be projected onto a target object. An initial pattern can be isomorphic, repeating a configuration of lines or dots over the extent of the pattern. Initial patterns may also be structured as an isomorphic repetition of one or more non-isomorphic patterns. The extendible nature of an isomorphic pattern or an isomorphic repetition of one or more non-isomorphic patterns enables an assessment of the target object beyond a portion of the target object that is within the line of sight. The original pattern management module 202 can also use an initial pattern that is partially or entirely non-isomorphic to uncover information regarding specific areas or aspects of the target object. According to aspects of the disclosure, the use of a combined isomorphic pattern with embedded non-isomorphic patterns allows identification of missing portions, hidden portions or holes. For example, using a pattern with an isomorphic repetition of the non-isomorphic double log pattern provides identification of the non-isomorphic pattern allows the system to detect missing elements of the overall pattern and the isomorphic pattern allows registration of the overall pattern to more easily scale and detect the missing parts of the non-isomorphic pattern. This combination allows the system to estimate within a reasonable accuracy the measurement of the hidden part of the object that caused the loss in the pattern.

In some embodiments, different initial patterns can be used for the same surface or different surfaces of the target object. The original pattern management module 202 can also determine additional initial patterns based on the result of projecting or placing existing initial patterns on the target object. For example, when the result of projecting an isomorphic pattern to an entire surface of the target object shows that a particular area of the surface is full of hills and valleys, the original pattern management module 202 can select a non-isomorphic, finer pattern to better capture the characteristics of that particular area. The selection can be made based on user selections, attributes of the target object, etc.

In some embodiments, the original pattern management module 202 determines that each initial pattern is to be implemented by a molding based on a user selection, for example. The molding can stand alone or be attached to the light source. The size of the molding can depend on the locations where the molding may be placed relative to the light source and the target object, the desired coverage by the projected pattern of a surface of the target object, or other factors. The molding can be made of any solid material that absorbs light without otherwise interfering with nearby lighting.

FIGS. 3-12 illustrate various initial patterns. They are further discussed as follows.

Pattern Type 1: Isomorphic Pattern of Identical Shapes

Figure 3:
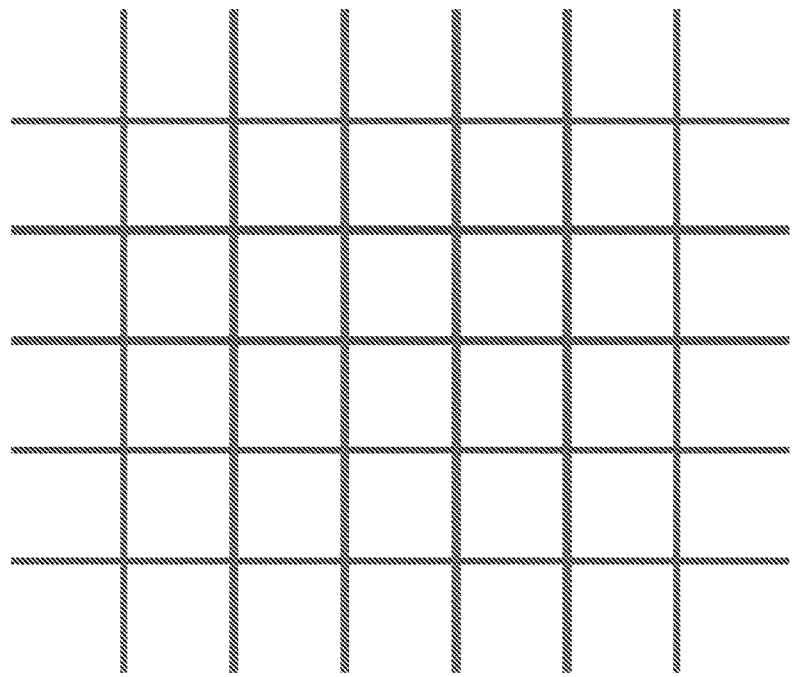
FIGS. 3-12 illustrate various patterns.
Figure 10:
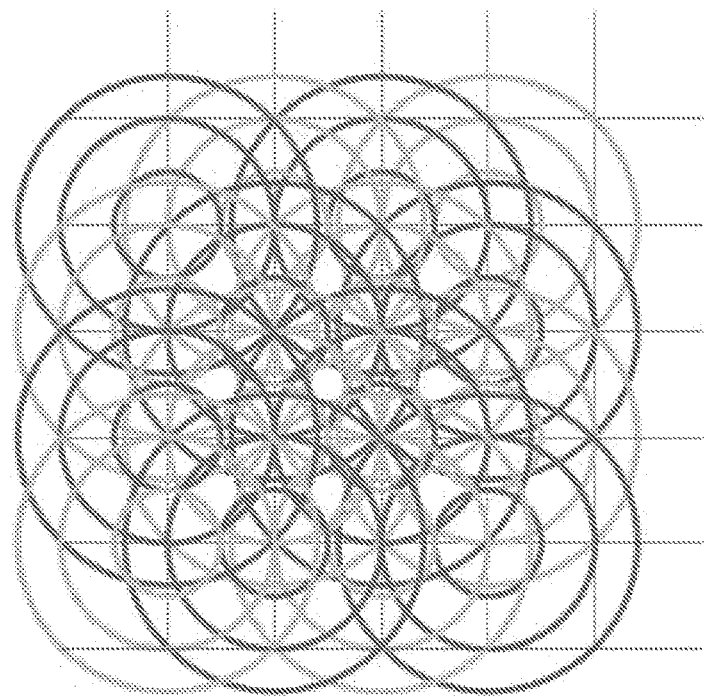
Figure 11:
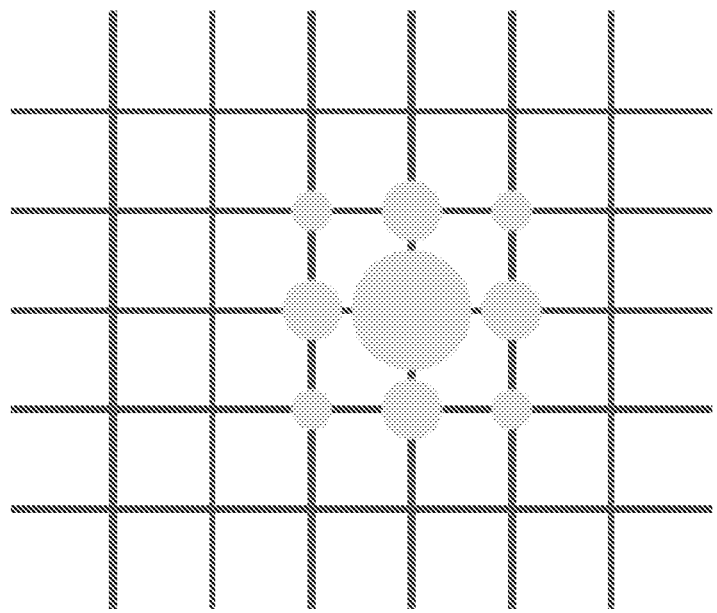
Figure 12:
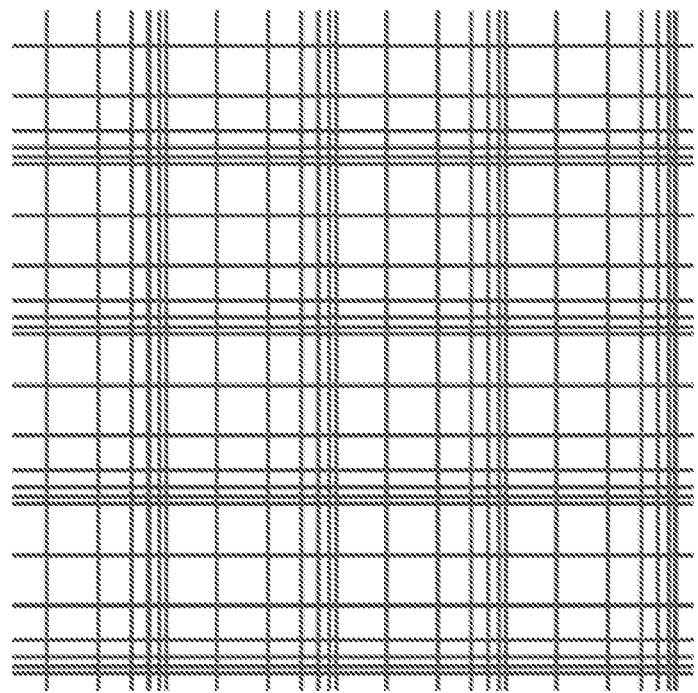

In some embodiments, this is the most basic pattern for measuring an object and. It is illustrated in FIG. 3; it is also illustrated in FIG. 10, which is a non-checkerboard isomorphic pattern of identical shapes. Each 2D geometric shape in the pattern is of a known size and is completely identical to every other 2D geometric shape in the pattern. Placing this 2D pattern on a 3D object (either via draping material printed with the pattern over the object so that it conforms to the surface of the underlying object or projecting the pattern onto the object, potentially from several points so that the pattern conforms to the surface, via an image projector or transparent image illuminated by a projection light) causes the pattern to distort based on the shape of the underlying object. The basic geometry of the pattern (geometric shapes of known dimensions) can then be used to determine the distance from the point of image capture to the object at every point of the pattern. This pattern works for objects that are completely convex in shape (relative to the point of image capture) or objects that have both convex and concave elements in their surfaces but which never have any part of the their surface hidden from the point of imaging the pattern.

In some embodiments, the pixel count in the lines of the pattern can be used, along with line length of lines within the shapes, to determine a rough distance from the point of imaging to any point on the underlying object and this can then be further refined by looking at the imaging focus setting which produces the sharpest line image. The distortion in each 2D geometric shape (line curvature and angle distortion in angles formed at the implied tangent lines at the vertices between 2D shapes—e.g. corners of adjacent squares for a pattern made out of a checkerboard of squares) can then be used to model the surface of the underlying object. When all such modeling tasks are completed over the extent of the pattern, the dimensions of the segment of the underlying object can be estimated.

Pattern Type 2: Isomorphic Pattern of Locally Y Dimension Non-Isomorphic Patterns In some embodiments, this type of pattern is formed by maintaining a regular pitch separating lines in one direction (for example the 'Y' dimension) and creating a cyclic change in spacing of lines in the other direction (continuing the example, in the "X" dimension). An example of this type of pattern is given in FIG. 4. The cyclic change creates a large pitch isomorphic pattern (i.e. the squares formed by each cycle in the "X" dimension pattern show an isomorphic pattern). Within each large square, the pattern is predictable but not isomorphic as the line space (i.e. pitch) is decreasing in a known way.

In some embodiments, this pattern measures all objects that the first pattern can measure. However, unlike the first pattern, this pattern can also be used for measuring objects that have surfaces that include segments that fold away and are hidden in the "X" dimension from the point of imaging. The non-isomorphic pattern within the larger isomorphic squares can be used to detect missing parts of the isomorphic pattern and accurately estimate how much of the isomorphic pattern has been missed in a local area. Using that information, the system can infer the measurement information concerning the object underlying the pattern. This type of pattern is therefore error correcting in the "X" dimension.

In some embodiments, since the initial shape and size of each bounded area within the pattern at any level (isomorphic or Non-isomorphic levels) is completely known, the system can compute the measurements of any part of the object over which this pattern has been placed and also infer the measurement of any part of the object which has hidden parts in the "X" dimension.

Figure 5:
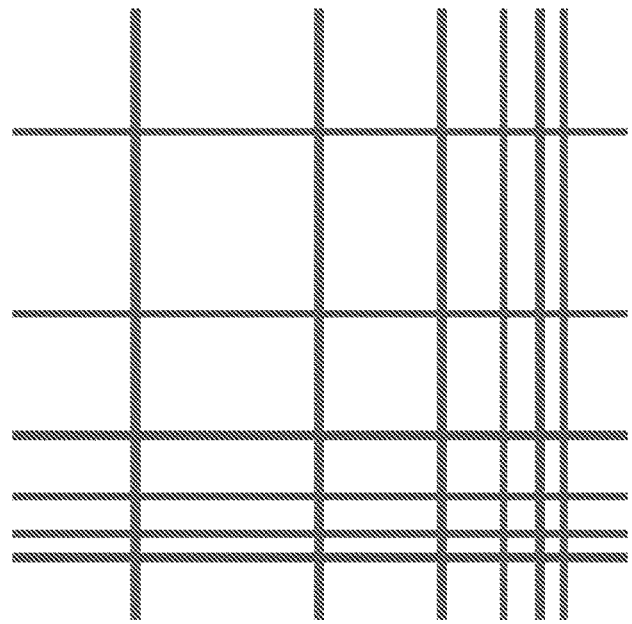
Figure 6:
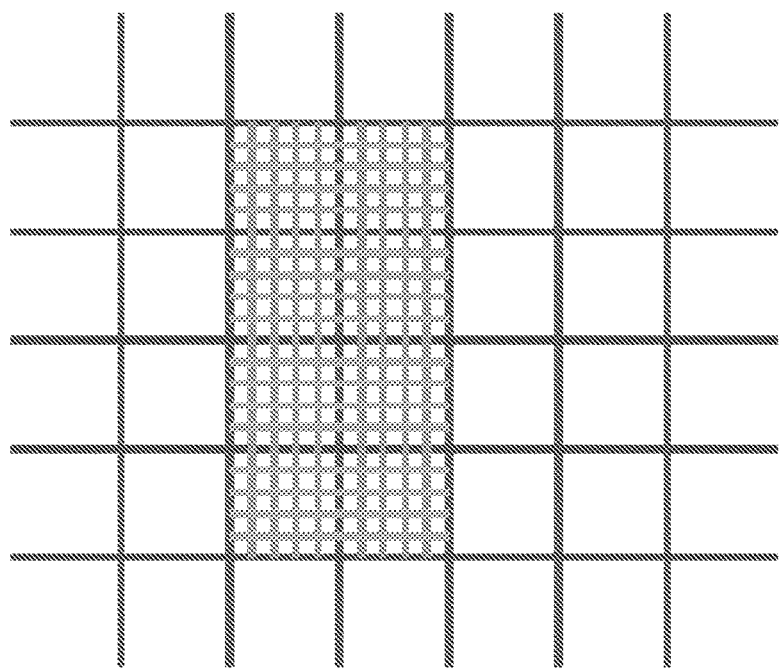
Figure 7:
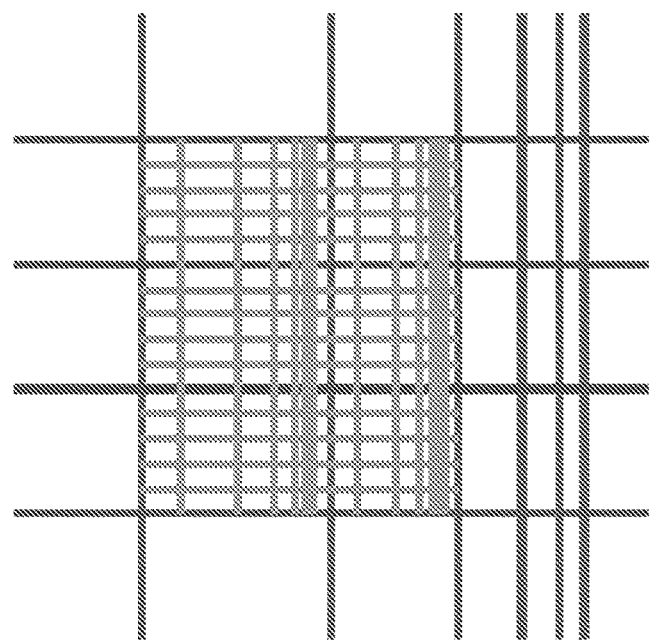
Figure 8:
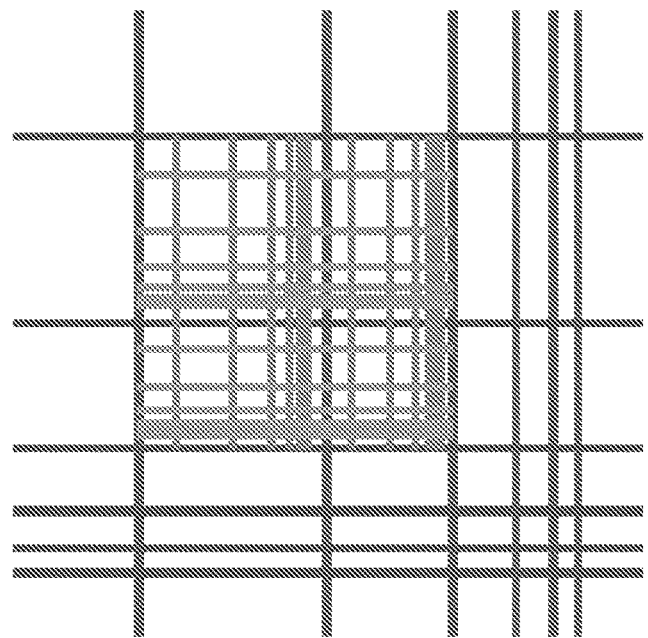
Figure 9:
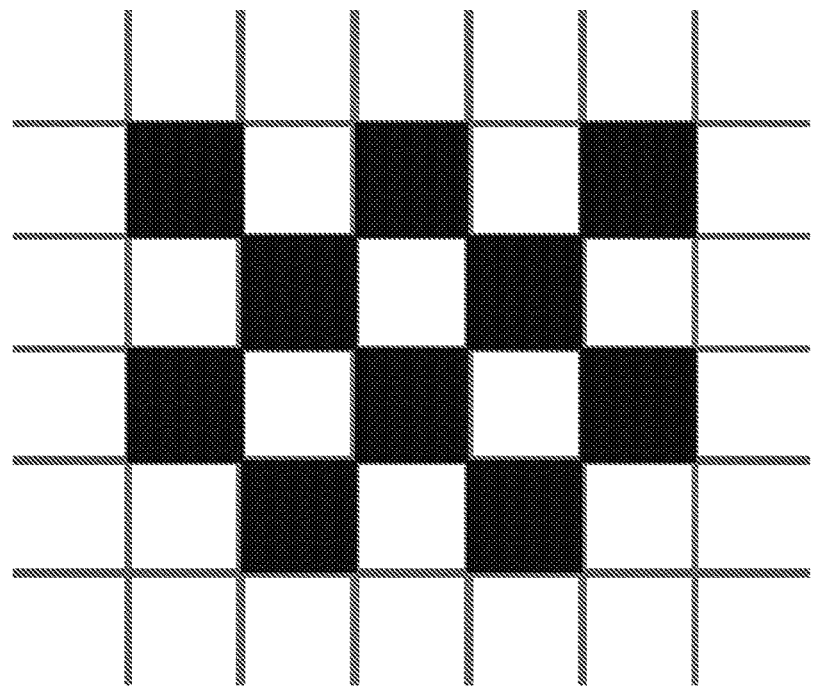

Pattern Type 3: Isomorphic Pattern of Locally X and Y Dimension Non-Isomorphic Patterns In some embodiments, instead of a cyclic variation in only the 'Y' dimension, a pattern can have a regular cyclic variation in the "X" dimension. The cycle can be the same frequency in both dimensions or difference in each dimension depending on any prior knowledge of the type or category of object to be measured. An example of this type of pattern is illustrated in FIG. 5.

In some embodiments, there is a larger scale isomorphic pattern that can be detected out of the naturally occurring large squares formed by the cyclic placement of the lines in the "X" and 'Y' dimensions. As with the previously discussed pattern types, these lines and the known geometric shape they found can be used to determine distance and model the surface underlying the pattern. Pixel count, line distortion and angles, or tangent angles, where the lines intersect all provide sufficient information to accurately model the underlying surface.

In some embodiments, the cyclic nature of the line placement in both the "X" and 'Y' directions allow this type of pattern to be used to accurately estimate any part of the underlying object that is hidden from the point of imaging since the missing pattern elements can been detected using the cyclic nature of the pattern within the larger isomorphic squares. The process is the same as that used with a 'Y' dimension only cyclic pattern except that it can detect how much of the pattern cannot be seen in both directions either individually or simultaneously. Effectively these types of patterns feature error correction capability in both the "X" and 'Y' directions.

Pattern Elements: Cyclic Properties

In some embodiments, a regular 2D pattern with is isomorphic everywhere, as illustrated in FIG. 3, can be thought of as the trivial cyclic pattern with a frequency of 1 in both the "X" and 'Y' dimensions. This means that the line spacing the "X" dimension is constant and the line spacing the 'Y' direction is constant. While constant in each direction, the spacing in the "X" direction may be the same or different than the spacing in the 'Y' direction. When it is the same, the pattern is equivalent to a checkerboard of squares (technically it is a pattern of identical shapes that have all "sides" equal—in other words the each shape is symmetric about its X and Y axis and rotating each shape through 90 degrees would produce exactly the same shape and overall pattern). When it is different the patter is a checkerboard of non-square rectangles (technically it is a pattern of identical shapes for which opposite "sides" are equal in length—in this case each shape is symmetrical about its X and Y axis but rotating each shape through 90 degrees would produce an overall pattern that would be the original pattern rotated through 90 degrees).

Figure 4:
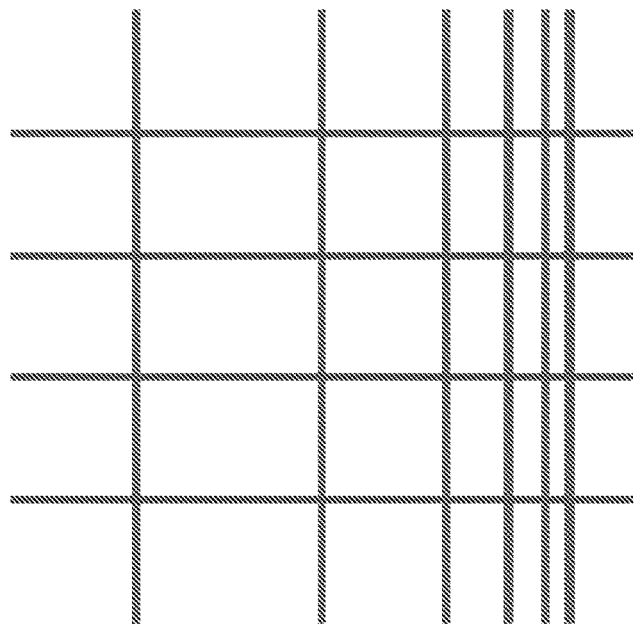

In some embodiments, a pattern with a cyclic frequency of 1 in both directions is completely isomorphic. A pattern with a cyclic frequency different from 1 in at least one dimension has both isomorphic and non-isomorphic properties, as illustrated in FIGS. 4 and 5. The frequency of the pattern determines the way in which the pattern repeats itself. That defines the "larger" isomorphic pattern and can be seen, for example, in FIG. 12.

In some embodiments, within each containing "square" the pattern is locally non-isomorphic due to the cyclic variation in line spacing. As can be seen from FIGS. 4, 5 and 10, such patterns can be made up of various sized rectangles or other shapes that change in size depending on the location in the overall pattern. It is helpful to know what these complex patters look like before being applied to a 3D objection.

In some embodiments, patterns are built using various mathematical constructs such as varying one or both dimensions in a logarithmic cycle. This allows the pattern to be predicted and obviates the need to measure every part of the pattern before it is placed on an object. The result is a simpler algorithm. However, any 2D can be used for this method of measurement so long as it covers all the area of interest of the 3D object and so long as it is sufficiently fine in detail to be able to provide measurements within the desired, acceptable tolerance. If the pattern is not mathematically constructed then it must be measured on a flat surface to provide the base reference point from which the software can later detect and measure distortions in the pattern when it is placed or projected onto a 3D objection. The algorithm for using non-mathematically generated patterns is much more complex and more compute intensive as it potentially has to treat each part of the pattern uniquely.

Pattern Elements: Shapes

In some embodiments, constructing a pattern out of a series of known, recurring shapes offers a great deal of analytic and computational efficiency. In addition to the actual dimensional computation, the nature of the shape can determine the ease with which the shape and overall pattern can be imaged—i.e. captured by an imaging sensor and then extracted from the image to eliminate unwanted image elements and/or noise.

In some embodiments, shapes which start with straight lines for sides and known angles between sides are the easier to deal with. These are followed by shapes that are composed of arcs that are well defined as sections of circles. An example of that type of pattern is given in FIG. 10. In both cases, any distortion in the shape that results from placing the shape on a 3D object will convey an enormous amount of dimension/volume related data that can be extracted and computed relatively quickly.

In some embodiments, the measurement method is not limited to such regular shapes. Any tessellation of a 2D plane made out of any shapes that provide complete coverage to the plane can be used. The caveat is that the compute power needed for irregular shapes or randomness in the repetition of shapes increases dramatically when the entire surface needs to be piecewise analyzed each time it is used to measure a 3D object.

In some embodiments, the more efficient shapes are those that can be constructed using an algorithm based on mathematics that yields an isomorphic pattern containing non-isomorphic sub patterns with a known cyclic nature and which repeat in a known way to yield the large scale isomorphic nature of the overall pattern.

Pattern Elements: Varying Density, Shape and/or Cycle in One or Both Dimensions

In some embodiments, a pattern is essentially a single replicated isomorphic pattern that repeats the placement of either an isomorphic or non-isomorphic sub-pattern. One key property of this is that no matter where you are in the overall pattern, its global isomorphic nature means that the current locale appears the same as any other locale one might chose. However, that nature is not needed for this method to work nor is it the ideal solution in all cases of apply the method.

In some embodiments, if the method is going to be applied to a class of objects that may each be a variation on a known theme then taking into account the underlying "theme" of the objects may allow a pattern to be used that varies in line density or shape to refine measurement in areas of distortion or critical shape changes for that set of objects. For example, if the object being measured is a human torso then increasing the density (i.e. effective number of lines/objects) of the pattern in the area of the shoulder or hip would yield more measurement data for those areas of critical curvature. Conversely, using a sparse pattern across a back would yield sufficient observation data while reducing the number of computations necessary to create the measurement data thereby reducing either compute time or system compute performance requirements.

Pattern Elements: Color

In some embodiments, black and white patterns work well. However, so do patterns in any color or selection of colors. The critical element is the contrast between the pattern and the background on which the pattern is printed or projected. The contrast needs to be great enough for the image processing to identify and extract the pattern.

In some embodiments, as a specific use of color, several patterns can be used simultaneously to improve accuracy. Each pattern would be printed or projected in a different, contrasting color. The software algorithm extracts each pattern from the image and carries out the measurement computations for each pattern. Comparison of results then yields a refined accuracy by computing the appropriate set of measurements based on those derived from each pattern (for example, the simplest solution would be to average the measurements obtained from each pattern).

In some embodiments, the pattern transformation module 204 manages the configuration of the shape measurement system for projecting a two-dimensional initial pattern onto the target object. The pattern transformation module 204 selects a light source, which can be a collimated light source, a pointed light source, etc. The pattern transformation module 204 also ensures that the light reaching the target object is visible. The visibility can be affected by the relative placement of the light source, the structure of the pattern molding, the shape and material of the target object, or other factors. Based on these factors, the pattern transformation module 204 can determine the colors, intensities, and other attributes of the illuminated light accordingly.

In some embodiments, the pattern transformation module 204 determines the distance between the light source and the pattern molding as well as the distance between the pattern molding and the target object. When a single initial pattern is used for one surface of the target object, the pattern transformation module 204 can arrange the light source, the pattern molding, and the target object to ensure that the projected pattern covers the entire surface of the target object. When multiple initial patterns are used for one surface, the pattern transformation module 204 can similarly arrange the components of the system to ensure that the multiple projected patterns combine to cover the entire surface of the target object.

In some embodiments, the pattern transformation module 204 selects a camera. It can be a standalone camera or one that is embedded in another computing device, such as a cellular phone, a tablet, a laptop computer, a desktop computer, or a wearable device. The pattern transformation module 204 then determines the placement of the camera relative to the light source and the target object generally to ensure that the camera clearly captures the projected pattern in its entirety. The distance to the target object in particular is useful to the computation of three-dimensional information performed by the distorted pattern processing module 206, as discussed below.

In some embodiments, the pattern transformation module 204 provides movement instructions to the target object for obtaining projected patterns on different surfaces of the target object. The pattern transformation module 204 coordinates the operation of the camera and the display screen to communicate with the target object. For example, the target object can be a human or an object operable by a human. Upon detecting the current appearance of the target object using the camera, the pattern transformation module 204 determines an appropriate movement instruction and communicates the movement instruction to the target object using the display screen. It also ensures that the design and presentation of the movement instruction enables accurate observation by the human receiving the movement instruction even from some distance away.

Figure 13:
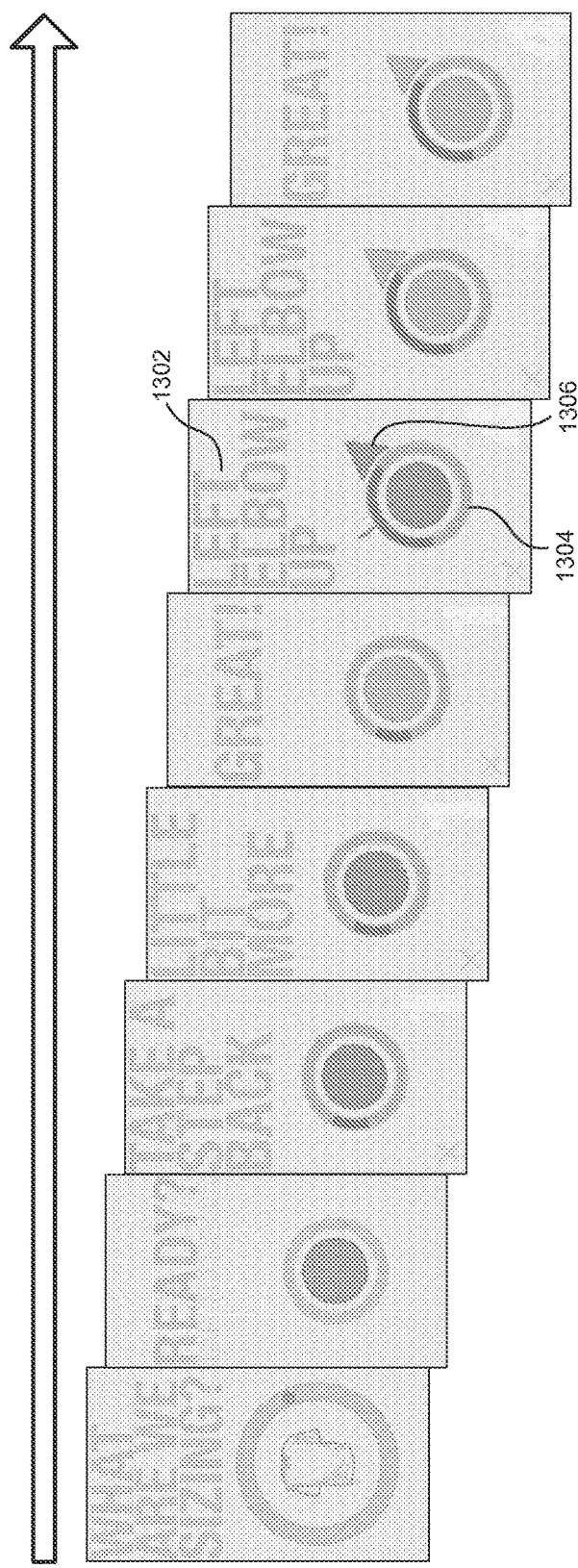
FIG. 13 illustrates example graphical user interfaces (GUIs) shown on a display screen of the shape management system for directing the movement of the target object.

FIG. 13 illustrates example graphical user interfaces (GUIs) shown on a display screen of the shape management system for directing the movement of the target object. The list of GUIs from left to right corresponds to a series of instructions shown to a person possessing or operating the target object during the course of communication with the person. In each GUI, there are a sufficiently simple and large geometric shape 1304, which is not entirely associated with any known object, for representing the target object and an easily identified direction indicator 1306 that instructs a movement. There can also be some text 1302 that is brief and in a large, clear-to-read font that corresponds to the graphics, namely the combination of the geometric shape 1304 and/or the direction indicator 1306. In one example, the geometric shape 1304 is a circle. Also in the example, the direction indicator 1306 is a triangle where two of the vertices slide along the circle, the current position of these two vertices indicates a specific portion of the target object, and the movement of these two vertices indicates a specific movement of the specific portion. The text states that the specific portion of the object should move in a certain fashion. When the shape measurement system incorporates a speaker, the pattern transformation module 204 can also coordinate the operation of the speaker to further facilitate the communication with the person by reading the text out loud, for example. Once an instruction in a GUI is displayed, a new posture or arrangement of the target object formed in response to the instruction is detected, and a new instruction is determined and displayed in another GUI until the appearance of the object is ready for the projection of an initial pattern and the capturing of the projected pattern.

In some embodiments, the distorted pattern processing module 206 first identifies a projected pattern from a camera image. The identification can be performed using various techniques known to someone of ordinary skill in the art. Some examples techniques that apply to color patterns are described below.

The system first converts Luminance from RGB to YUV:

$$\text{Luminance} = 0.21R + 0.72G + 0.07B$$

The system then applies appropriate (n,n) kernel pre-edge detection to eliminate high frequency anomalies such as cloth stitching, bleed, etc. An example would be a 2D Gaussian (7,7) blur filter, as opposed to an average filter which creates ripples (high frequency ringing).

Next, the system performs Edge detection using 2D Laplacian edge detector. The system can take gradient along any vector $\nabla f(x,y)$, threshold around peak, eliminate "fat peak" by computing Laplacian $\nabla^2 f(x,y)$, find zero crossings, and compute local variance to remove spurious/false edges.

Alternatively, the system can use a Canny Edge detector and thresholding. The system can also apply a Color edge detection for color variance patterns, as illustrated in FIG. 10.

Next, the system applies a Sobel filter on R,G,B components separately, in both dimensions. Let $(R_x, G_x, B_x)$ denote the RGB vector sobel filtered in the 'x' direction and let $(R_y, G_y, B_y)$ denote the RGB vector Sobel filtered in 'y' direction.

The system then computes the Jacobian and cross Jacobian, where $J_x = R_x^2 + G_x^2 + B_x^2$, $J_y = R_y^2 + G_y^2 + B_y^2$, and $J_{xy} = R_x \cdot R_y + G_x \cdot G_y + B_x \cdot B_y$.

The system then computes the first eigenvalue of $J' \times J = E_1$ and set the edge value to be $\sqrt{E_1}$. Thresholding results in a Binary image (0=black background) (1=white foreground).

From the black-and-white image containing the projected patterns, the system finds contours corresponding to the projected patterns using any technique known to someone of ordinary skill in the art, such as the contour tracing algorithm by Theo Pavlidis (Pavlidis. *Algorithms for graphics and image processing*. S.I: Springer, 2012. Print). In addition, the system closes the contour paths by joining two open ends of a contour as long as the Cartesian distance between the two open ends is within a specific window. The joining can be performed by any method known to someone of ordinary skill in the art, such as linear or quadratic interpolation or computation of a cubic spline using the $0^{th}$, Nth and N−1th points of the contour.

Upon obtaining the contours, the system performs additional computation that is useful for the determination of depth information for the target object. The system next computes moments for each contour and stores them for determination of the stretch of the initial pattern and the depth and shape of the target object.

The moment is computed by $m_{a,b} = \iint x^a y^b f(x,y) d_x d_y$. The zero$^{th}$ moment describes area of the contour is computed by $m_{00} = \iint f(x,y) d_x d_y$.

The first order moment contains the centroid (center of gravity) of contour, and it is computed as follows:

$$m_{10} = \iint x \, f(x,y) d_x d_y$$

$$m_{01} = \iint y \, f(x,y) d_x d_y$$

$$(x_{center}, y_{center}) = \left(\frac{m_{10}}{m_{00}}, \frac{m_{01}}{m_{00}}\right)$$

The Second order moments describe the semi-major and semi-minor axes, the orientation/tilt, and the roundness. Use of second moments of contours enables image registration where in image of the projected pattern is aligned with the known reference points in an image of the initial pattern through geometric transformations. Specifically, calculating the semi-major and semi-minor axes of an ellipse that bounds a closed polygon reveals the scaling of the shape in two orthogonal directions, thereby giving a localized stretch factor in the material. This stretch factor is characterized and a depth is computed for that localized region as a function of it (which may be computed or tabulated), as further discussed below.

Figure 14:
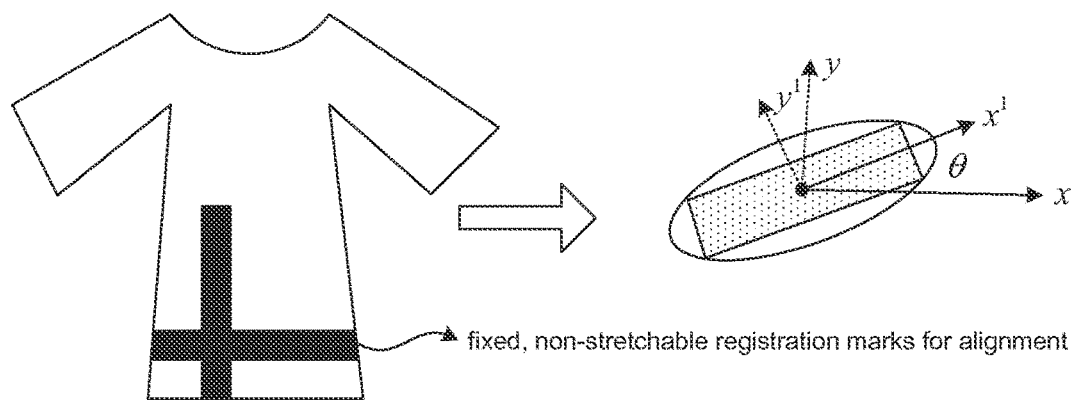
FIG. 14 illustrates an example scenario where the computation of moments enables image registration.

FIG. 14 illustrates an example scenario where the computation of moments enables image registration. The amount of misalignment θ can be represented as follows, where the second order moments are represented by $(x^1, y^1)$ and the reference coordinates are represented by $(x, y)$: The angle θ determines the orientation or tilt of the local shape/polygon. It can reveal how the gradient of the shape formed by all the polygons is rolling off to an edge, which is further confirmed after analyzing neighboring polygons.

$$\theta = \frac{1}{2}\tan^{-1}\left(\frac{2m_{11}}{m_{20} - m_{02}}\right)$$

Figure 15:
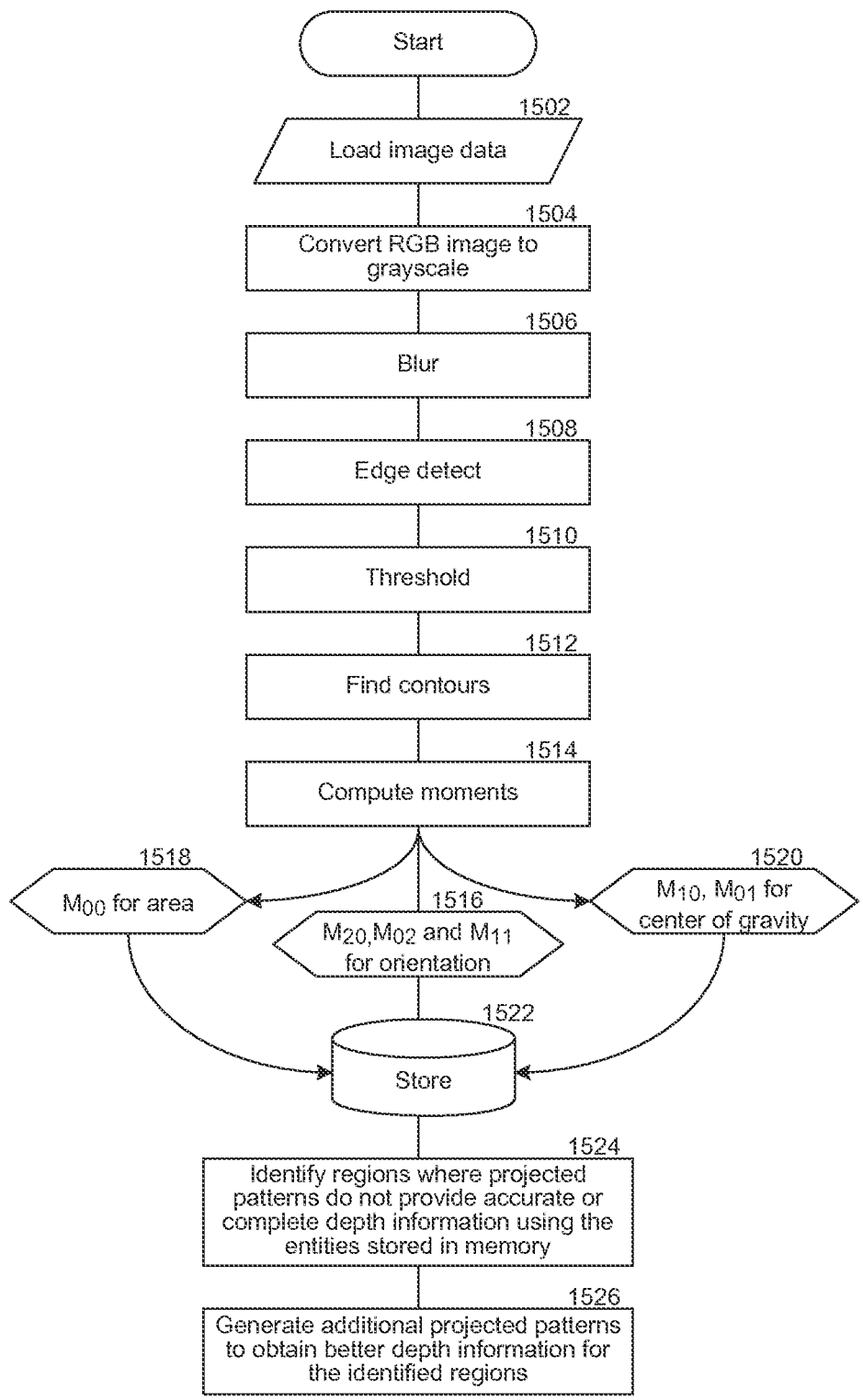
FIG. 15 illustrates an example process in which the system obtains and refines projected patterns.

FIG. 15 illustrates an example process in which the system obtains and refines projected patterns. In step 1502, the system obtains a color image containing the projected patterns. In steps 1504-1510, the system obtains a black-and-white image corresponding to the color image. In step 1512, the system extracts the projected patterns. In steps 1514-1520, the system computes various entities for estimating depth information for the target object, such as the contour area, the center of gravity in each pattern unit, and the moments. In step 1522, the system stores the computed entities in memory. In step 1524, the system identifies regions where projected patterns do not provide accurate or complete depth information, and computes associated error or confidence scores, using the entities stored in memory. In step 1526, the system generates additional projected patterns based on the confidence scores and other factors to obtain better depth information for the identified regions. The system can repeat the last two steps until satisfactory depth information for the entire target object.

In some embodiments, the distorted pattern processing module 206 then examines the projected pattern to derive three-dimensional information regarding the target object. The amount of local change in the projected pattern from the initial pattern is proportional to the depth information that constitutes the third dimension. When the initial pattern is a grid, the distorted pattern processing module 206 measures the number of pixels between grid lines (or area in each local pattern) in the initial pattern. The distorted pattern processing module 206 also measures the number of pixels in the projected pattern as viewed by the camera, and determines any distortion in the lines within the pattern and the 2D shapes enclosed by these lines. The distorted pattern processing module 206 can then use the difference of the two pixel counts along with the distortion or shape change in the lines and enclosed shapes, to estimate the depth and shape corresponding to the surface covered by the patterns, as further discussed later in the application.

According to aspects of the invention various types of known patterns may be used. The difference to the pixel count per inch is a function of the distance of the surface of the target object from the camera. The pixel count is the prime measure measurement of the depth of the object's surface relative to the camera: as the surface varies up and down it effectively varies closer or away from the camera and makes slight changes in the pixel count per inch of the object. Since the pattern is known, that count of pixels per inch coupled with sensing the line and enclosed shape distortion in the object gives the measurement of where the visible parts of the surface is located relative to the camera at any given point. Repeating a non-isomorphic pattern within the framework of an isomorphic pattern allows the system to use the measurements surrounding an occluded part of an object to estimate measurement of the any such occluded part of the object within an acceptable error tolerance.

Figure 16:
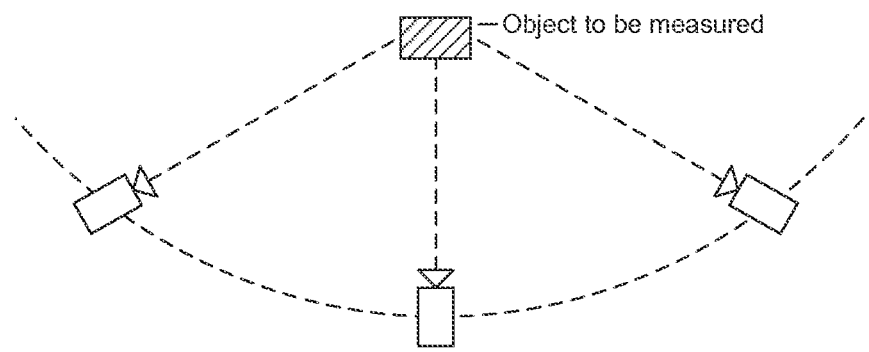
FIG. 16 illustrates an example setup of the target object with respect to one or more cameras.

FIG. 16 illustrates an example setup of the target object with respect to one or more cameras. This setup leads to multiple measurements from different viewpoints, which can detect and reconcile pattern loss, especially with respect to complex surfaces. In some embodiments, the objects can be imaged from different angles.

Given grid matrix denoted as U with grid points $U_{ij}$, distortion in a projected pattern from an initial pattern denoted as $\hat{U}$ at grid points $\hat{U}(i,j)$ occurs when an object enters the field-of-view. When there is no distortion, i.e., U=U, the depth Z at grid points $Z_{ij}$ is 0. In some embodiments, given any pattern grid $U, Z_{ij}$ is assumed to be 0 when there is no object in the field of view.

Figure 17:
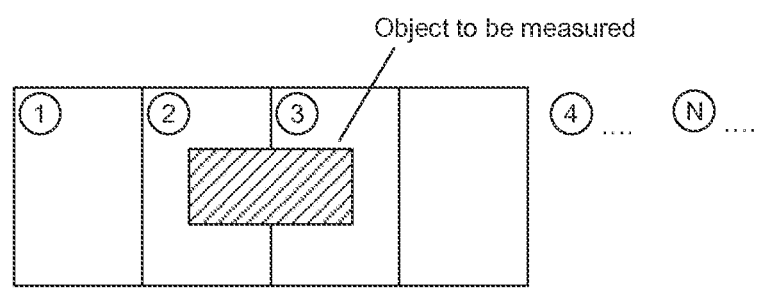
FIG. 17 illustrates an example scenario where the depth measurement is repeated at positions 1-N around the projected pattern.

FIG. 17 illustrates an example scenario where the depth measurement is repeated at positions 1-N around the projected pattern. In some embodiments, the depth computation process can be repeated across multiple points on the projected pattern, resulting in a Matrix ID with elements $d_{ij}$ corresponding to 2D coordinates $U_{ij}$. As a set, (UI, ID) represents a Cartesian coordinate system and in turn a 3D coordinate system across which a 'mesh' or a mathematical model for the target object can be applied.

Figure 18:
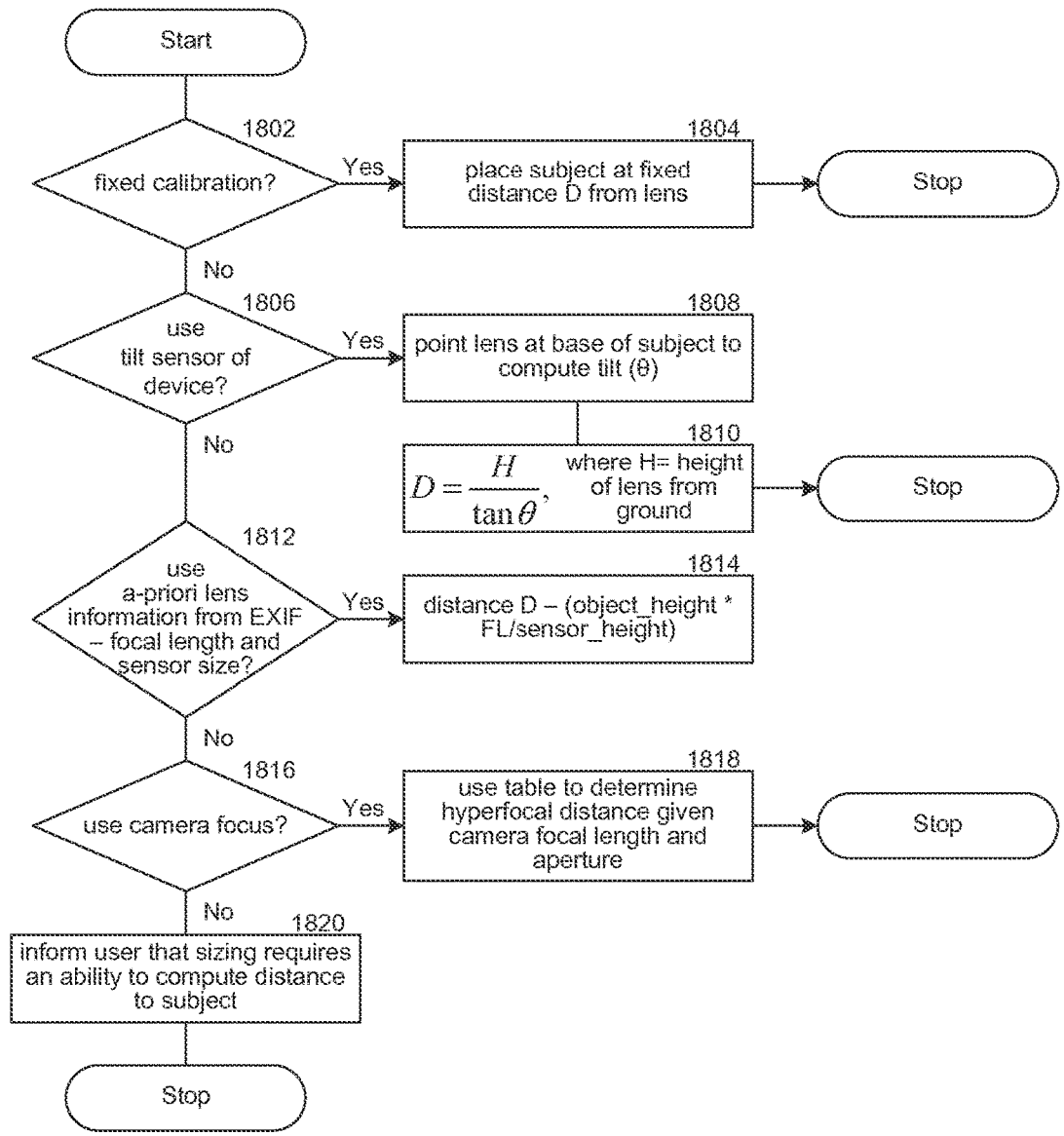
FIG. 18 illustrates an example process of determining the distance of the target object (or a reference point thereof) from the camera, which can be used to determine the depth information of the target object, (D) prior to sizing the target object.

FIG. 18 illustrates an example process of determining the distance of the target object (or a reference point thereof) from the camera, which can be used to determine the depth information of the target object, (D) prior to sizing the target object. In some cases, D may be known, as in steps 1802 and 1804, or may be computed using simple trigonometry, as in steps 1806-1810. In some cases, D may be calculated from the object size, sensor height, and the focal length of the camera lens, as in steps 1812 and 1814, which is further discussed below, or may be determined through aperture tables for the particular lens, given the focal length and aperture of the lens, as in steps 1816 and 1818. In the event that none of these methods or generally known methods can be performed, the user must be informed that sizing cannot be completed without being able to compute this distance, as in step 1820.

Figure 19:
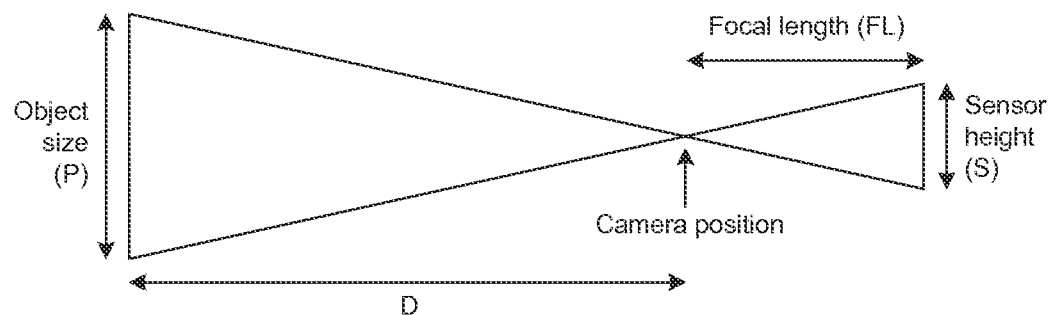
FIG. 19 illustrates the relationships between the camera lens, the camera sensor, and the target object.

In some embodiments, the computation of the distance D from the camera is determined from the sensor and lens information, as in step 1804. The vertical sensor size (S) and focal length (FL) of the lens determine the field of view angle that is an equivalent angle for a triangle representing the object size (P) and distance (D) from the lens. In this method, D=P*FL/S, which assumes the object fills the full vertical view. This is illustrated in FIG. 19.

For a projected pattern, which is distorted and corresponds to a depth Z of the target object, the depth Z is computed as $D*(1-(n/n'))$, where D is the distance of the sensor to the undistorted pattern, n' is the pixel distance between grid lines in a projected pattern and n is the pixel distance between grid lines in the initial pattern.

Figure 20:
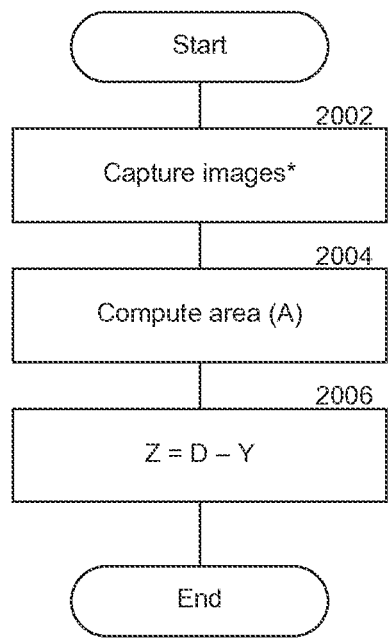
FIG. 20 illustrates an example approach for estimating the depth of a point on the target object using contour areas.

FIG. 20 illustrates an example approach for estimating the depth of a point on the target object using contour areas. In some embodiments, as an alternative approach, the area of a contour is used to determine the depth information of the points in the contour. In step 2002, the system captures a set of images of the projected pattern(s) on the target object. In step 2004, the system computes the contours in the projected patterns, as discussed above. The difference between the contour area obtained from a projected pattern and an original area obtained from the initial pattern is generally proportional to square of the distance between the camera sensor and the target object, namely Y. In step 2006, the system then computes the depth corresponding to the area of the contour as D−Y, where again D is the fixed distance between the sensor and the undistorted target, and Y is the computed distance of the target to the sensor.

Figure 21:
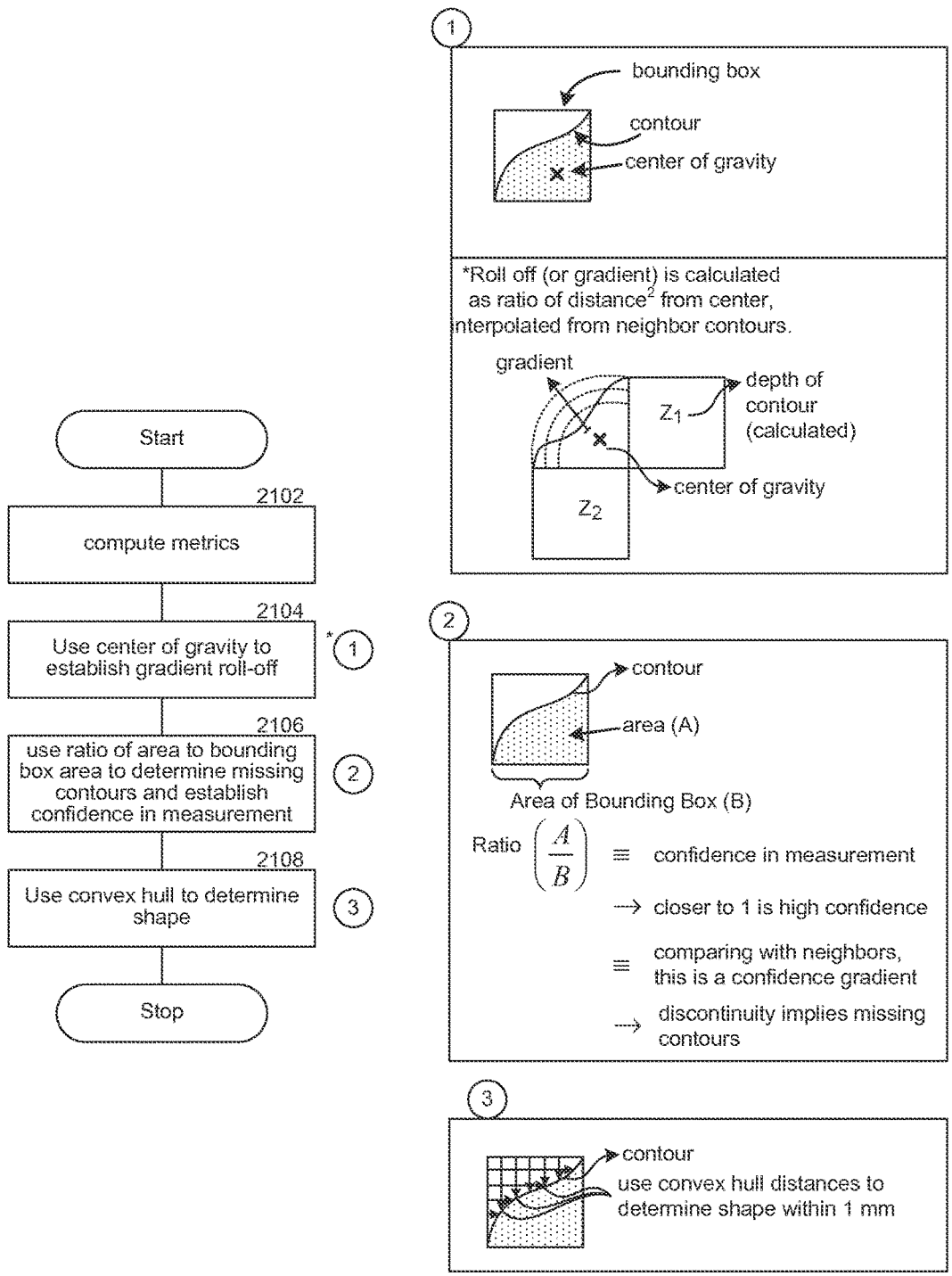
FIG. 21 illustrates an example approach of identifying areas of an initial pattern where refinement is desirable.

FIG. 21 illustrates an example approach of identifying areas of an initial pattern where refinement is desirable. In step 2102, for each unit of the initial pattern, such as a grid square, the system computes various metrics, such as the contour, the center of gravity or the moments in the corresponding unit of the projected pattern, as discussed above. In step 2104, the system identifies any potential gradient roll-off in the contour based on the center of gravity and depth information regarding this unit and neighboring units. The center of gravity is used as the centroid(x, y) coordinate to which the depth is assigned. Neighboring centroids reveal how the depth changes, and therefore establishes a gradient roll-off that can be used as an indication of contour continuity and thus depth continuity. In step 2106, the system determines the ratio of the contour area to the unit area as a confidence score for the existing depth information. When the confidence score is close to 1, the system then determines whether discontinuity exists. In addition to the gradient roll-off, various methods can be used to identify discontinuity, such as, calculating rate of change of slope ($2^{nd}$ derivative of the 3D mesh coordinates resulting in the rate of change of the slope), which would abruptly change in the event there's a discontinuity. In step 2108, when the determination indicates that a discontinuity exists, the system can remove the discontinuity and thus recovering depth information for the portion of the target object causing the discontinuity, by employing a median filter and performing interpolation, for example. When the determination indicates that no discontinuity exists, the system builds a convex hull using any technique known to someone or ordinary skill in the art. The convex hull can be used to assess the shape of the target object in multiple directions and thus refine the depth information, in the event the contour severely differs from the corresponding region in the initial pattern. When the confidence score is not close to 1, the system also builds a convex hull to establish a gradient roll off pattern and potentially refine the contour.

Figure 22:
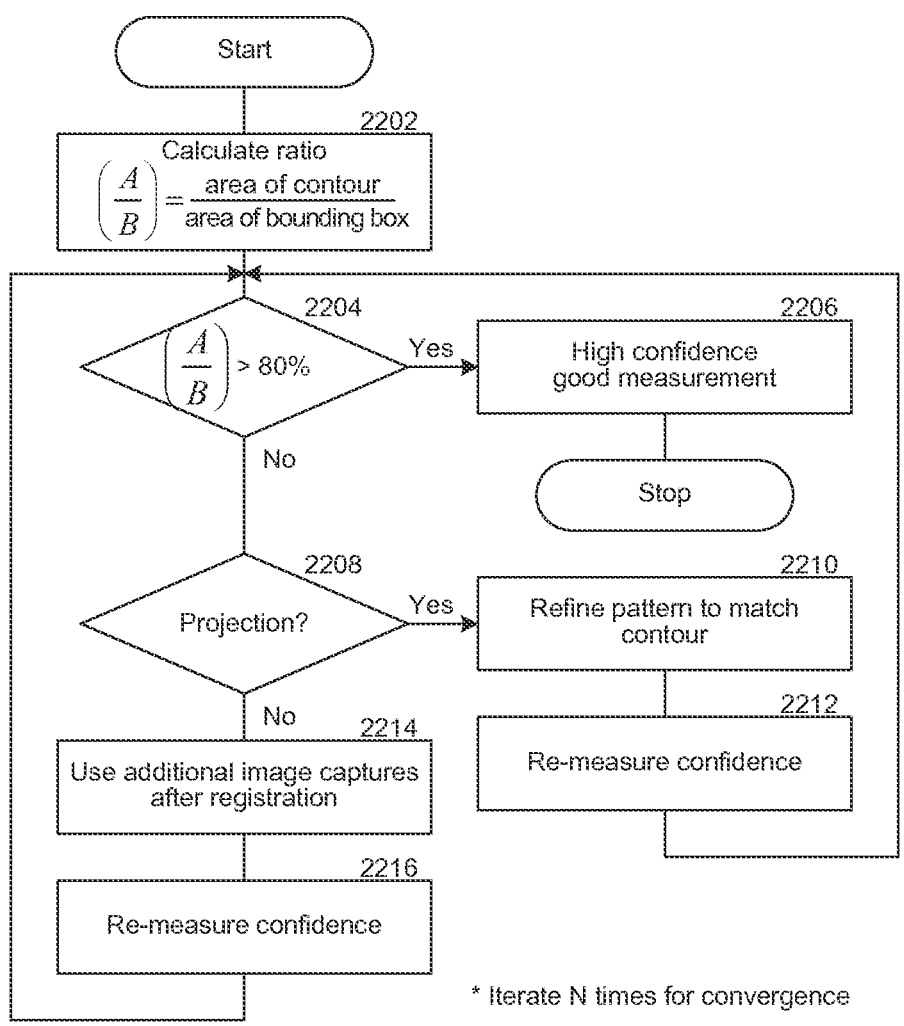
FIG. 22 illustrates an example approach of using confidence levels to adjust the pattern refinement process.

FIG. 22 illustrates an example approach of using confidence levels to adjust the pattern refinement process. In some embodiments, a refinement of the pattern is sought in high frequency areas (areas of high variability due to roll-off, concave or convex nature). To determine when a refinement is necessary, one such method is to compute a bounding box over each distorted local pattern. The ratio of the area of the local pattern (A) to bounding box area (B) as computed in step 2202 is compared with a predetermined threshold, such as 1 or a value close to 1, as in steps 2204 and 2206. When the ratio is much less than 1, a refinement is necessary. This ratio, when further away from '1' represents an error in measurement the extent of which is 1−A/B. Since it is determined that an error exceeds some known threshold, it is determined whether the distorted pattern was generated from light projection or an outfit being worn as in step 2208. The initial pattern is adjusted and the object is re-imaged for sizing as in steps 2210 and 2212, when the projected pattern is formed through light projection. Additional image captures can be necessary to increase the confidence level, especially when the projected pattern is formed through outfit fitting, as in steps 2214 and 2216. To ensure convergence, the ratio of 80% in 2204 may be successively relaxed, or a maximum number of iterations may be established. Along with each final measurement, a confidence level is also available which allows the user to augment this entire process with manual measurement in that region, if necessary. This process can be applied globally to validate previous measurements. An average, weighted average (or other) can be used for final measurement. In addition, several overlaid patterns can be used to accomplish the same result.

FIG. 23 illustrates how the depth of a point on the target object can be computed from various features of the projected pattern. While not all features contribute equally to the depth (Z) of the object (nor are they orthogonal), they all have an impact to refine the measurement. While not all features contribute equally to the depth (Z) of the object (nor are they orthogonal), they all have an impact to refine the measurement. The change in area between the initial undistorted pattern and the final distorted pattern as computed above is the most significant term in computing the depth of the target at that point. Closely related to the area is distance between grid lines which also computed above, yields results that contribute significantly to the depth of the target at that point. Area, as opposed to distance between grid lines, is generally a better measure as it allows for keeping other factors in the equation somewhat orthogonal to it, since distance between grid lines can change rapidly—which is better captured as a separate feature (e.g. convex hull). The centroid can be used to perform sub-pattern interpolation within each local region. The bounding box can be used to assess the roll-off based on the covered area of the local pattern vs. the bounding box area. The convex hull measurements can be used to assess the shape of the roll-off in multiple directions, in the event the bounding box severely differs from the underlying pattern. Finally, the curvature (orthogonal to area growth) is parameterized based on the nature of the material (and is therefore only relevant in non-projection cases), and is approximated by using the semi-major and semi-minor axes length difference for an elliptical bounding box. Based on various materials and objects being imaged, a weighted arithmetic average of the parameters is chosen to determine the depth and shape of a local pattern, and therefore the depth and shape of the underlying object.

It is the combination of the various image analysis methods together with the patterns described herein that allow this system to gain information, for example dimensional measurement, of arbitrary 3D objects. Patterns which are isomorphic patterns of locally non-isomorphic patterns (for example, FIG. 12 in which an isomorphic pattern that is locally non-isomorphic has been created using non-isomorphic patterns of the type shown in FIG. 5) are the key to gaining information from objects which have portions of their surface not visible from the point of view of the imaging device. When such a pattern is placed on such an object using, for example, a conformal fabric printed with the known pattern, then the parts of the pattern than cover the hidden part of the object are no longer visible from the imaging device. The image analysis algorithm described herein takes note of the missing parts of the pattern and uses the combination of isomorphic and non-isomorphic nature of the known pattern to compute how much of the pattern cannot be seen. Dimensional information can then be approximated from that information combined with the boundary dimensional information that is directly computed from the parts of the object that surround any part that is not directly visible. Thus this message is well suited to provide reasonably accurate dimensional measurements of any 3D object This process of using an isomorphic pattern of locally non-isomorphic patterns to compute dimensional information for 3D objects also works in the case of embodying this method using projected patterns. In this embodiment, the same, known pattern is projected and the resulting surface pattern on the object is captured from several different locations. In this case, the algorithm will see discontinuities the resulting pattern on object's surface surrounding the areas of the object that are hidden from the point of pattern projection or image capture. This is facilitated by the locally non-isomorphic properties of the projected pattern which yield not only the distance information but also the discontinuity information. By comparing the results from several difference viewpoints a reasonable estimate can be made of the dimensional measurements of the underlying 3D object.

In some embodiments, the distorted pattern processing module 206 determines a range of error tolerance, which can depend on the properties of the light source, of the camera, or of the target object. For example, when the target object is a human, one factor to consider is the breathing pattern, which affects the shape of the human body albeit to a slight degree. The distorted pattern processing module 206 can instruct the human to hold their breath during the pattern projection or can tolerate an error in a range that corresponds to the moving up and down of the human chest. Conversely, for applications in which static measurement is not required, the system can effectively measure the effect of motion on the object, for example the rate and/or depth of respiration. Similarly, for example, when the target object is the snow on the roof, the system can not only measure the depth of the snowfall and the shape of the snow drift on a roof but an also measure the rate of increase/decrease in depth and shape of the overall show covering as either more snow falls or snow melts.

Furthermore, as an isomorphic pattern can be used to reveal information regarding an invisible portion of the target object, that information can be cross-referenced with information directly obtained from projecting an initial pattern on the portion when it becomes visible to reduce errors and increase confidence levels. This process can also help refine the calculation of the properties of an invisible portion using the extendible nature of an isomorphic pattern.

In some embodiments, the distorted pattern processing module 206 can detect the rate of curvature of an object and the resulting rate of change in the depth of the 3D object relative to the camera. Depending on the accuracy needed by the end application for the data being gathered, this information can therefore be used to select areas of the object that require a finer-grained analysis and the initial pattern can be modified or replaced by a pattern that has increased pattern density in the areas of the object that the system determined required more detailed analysis.

In some embodiments, the distorted pattern processing module 206 displays the computed three-dimensional information regarding the target object to a user of the system, which includes coordinates of the measured surfaces of the target object. The distorted pattern processing module 206 can further convert these coordinates into sizing information with respect to a wearable piece for the target object. For example, when the target object is a person's upper body, the sizing information can be related to a shirt that is specified in terms of certain portions of the person's upper body, such as the neck, the chest, the shoulders, or the arms, and available from an external source, such as but not limited to an external database, application, cloud service, web service or server. By comparing the three-dimensional information of the person's upper body with the sizing information related to the shirt, the distorted pattern processing module 206 can identify the closest size of the shirt for the person and tailoring options based on the differences between the two pieces of information. The identified information can then also be displayed to the user.

Figure 24:
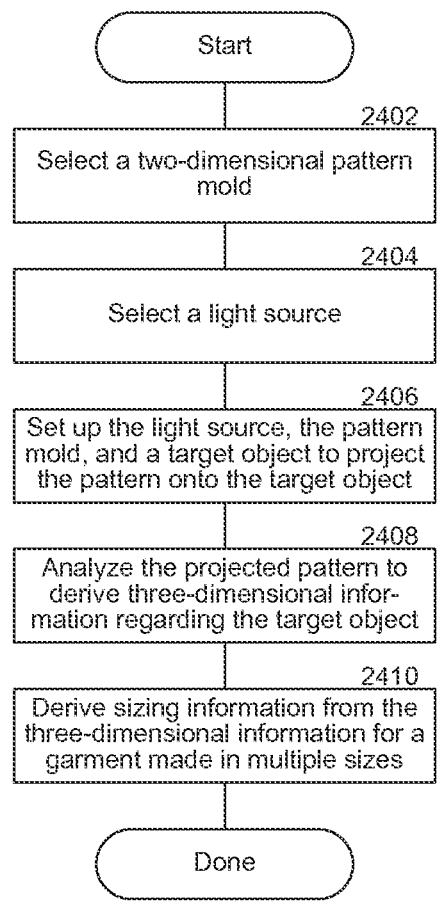
FIG. 24 illustrates an example process performed by the shape measurement system of projecting a two-dimensional pattern on a three-dimensional target object and analyzing the projected pattern in two dimensions to obtain three-dimensional information regarding the target object.

FIG. 24 illustrates an example process performed by the shape measurement system of projecting a two-dimensional pattern on a three-dimensional target object and analyzing the projected pattern in two dimensions to obtain three-dimensional information regarding the target object. In step 2402, the system selects a molding embodying a two-dimensional initial pattern. The initial pattern can be largely isomorphic, an isomorphic repetition of one or more non-isomorphic patterns or it can have a specific structure for a specific area or aspect of the target object. One or more initial patterns can be selected for the same surface or different surfaces of the target object. In step 2404, the system selects a light source. The light source can provide pointed light, which is easy to find, or collimated light, which makes the projected pattern easier to characterize. In step 2406, the system determines the relative placement of the different components of the system and the target object such that the initial pattern is properly projected on the target object and captured for further analysis. The system can provide instructions to be displayed so that the target object makes movements for better pattern projection and capturing. In step 2408, the system captures and analyzes one or more projected patterns to obtain three-dimensional information regarding the target object. The system can infer information even for an invisible portion of the target object. It can also cross-reference data extracted from different projected patterns to increase the accuracy of the analysis. In step 2410, which is often an optional step, the system further converts the three-dimensional information into sizing information with respect to a wearable piece available in different sizes. This feature can be helpful when the target object is a portion of the human body, where the wearable piece can be clothes, glasses, hats, jewelry, belts, shoes, hair accessories, etc.

Figure 25:
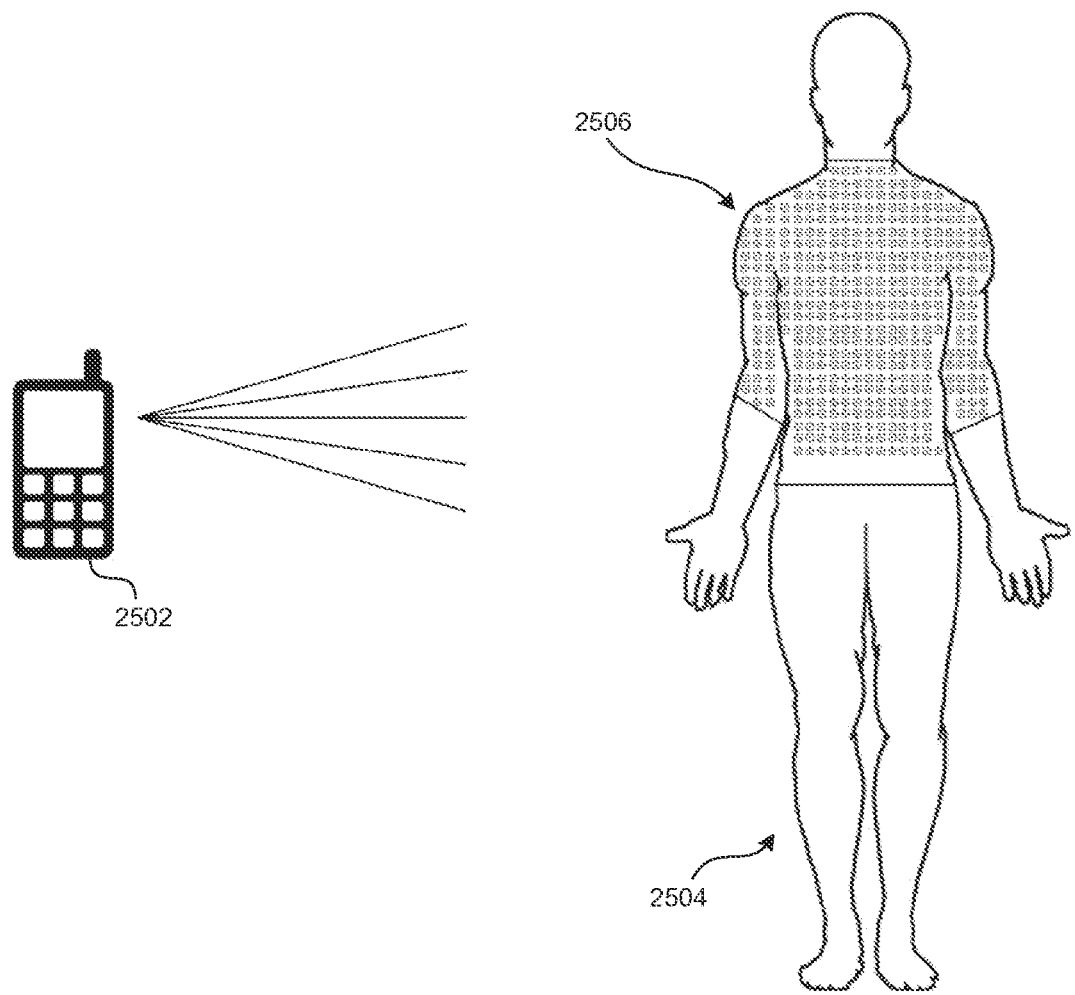
FIG. 25 illustrates another example setup of the shape measurement system.

FIG. 25 illustrates another example setup of the shape measurement system. In some embodiments, the system includes an outfit 2506, such as a shirt, with a two-dimensional initial pattern printed on it to be worn on a target object 2504, such as a human body. The system also includes a camera 2502, a processor and memory, and a display screen, which can be combined in a single device, such as a cellular phone. As the outfit is worn, the fabric stretches, and the initial pattern also stretches into a distorted pattern, which is in a way "projected" onto the target object and can be analyzed to derive three-dimensional information regarding the target object as described above.

In some embodiments, the original pattern management module 202 determines that the initial pattern is instead to be printed on an outfit to be worn. The original pattern management module 202 can choose from a variety of types of fabric which stretch to track the surface of the object in the outfit. It can also choose from a variety of shapes for the outfit depending on the shape of the target object and other factors. For example, the outfit can fit a specific portion of a human body or have one of the basic geometric shapes. For each of the shapes, one or more sizes can be available. Another choice to be made by the original pattern management module 202 is a printing technique that ensures that the pattern stretches evenly when the fabric stretches. According to aspects of the disclosure, "printing" would generally be using two processes: either the pattern is woven/knitted into the fabric as it is manufactured or is screen printed onto and into the fabric. As in the situation where the initial pattern is projected onto the target object by a light source, the original pattern management module 202 sets the colors and contrast of the initial pattern and the rest of the outfit such that the projected patterns can be accurately captured by a camera.

In some embodiments, the pattern transformation module 204 selects a calibration chart, which can be represented as a ruler, a grid, a chart, or any other suitable form that enables image registration. The calibration chart typically comprises a distinct, simple, and small pattern, which may or may not be replicated in several locations relative to the overall pattern, whose distortion is easy to detect and measure. The calibration chart can be used in a way to ensure that the camera capture would be successful. For example, the calibration chart can be designed such that when it is visible to the human eyes, it would be visible to the camera lens. The calibration chart can be incorporated in the outfit together with the initial pattern, or it can be implemented in a standalone device and placed nearby the target object at the time of image capture, so that an image of the calibration chart or a distorted version thereof can be captured together with the distorted pattern corresponding to the initial pattern.

In some embodiments, the distorted pattern processing module 206 performs a calibration process utilizing a specific calibration chart. Depending on how the calibration chart is implemented, the distorted pattern processing module 206 determines the distance of the calibration chart to the camera, which is helpful for further determining three-dimensional information regarding the target object. According to aspects of the disclosure, knowing the original size and layout of the calibration chart, its distance from the camera can be estimated using method [0074], the calibration chart measures the local distortion of the calibration chart caused by the fabric stretch. Since the overall pattern is also measuring the same distortion, the two taken together can be used to eliminate the distortion due to fabric stretch unrelated to depth variation on the object.

Figure 26:
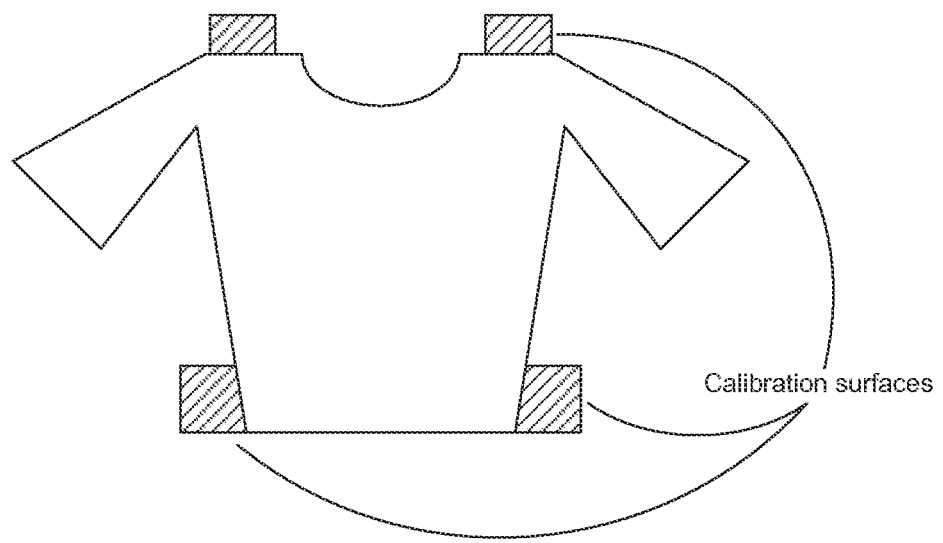
FIG. 26 illustrates an example outfit where calibration charts are incorporated.

FIG. 26 illustrates an example outfit where calibration charts are incorporated. In some embodiments, several calibration charts are placed on or incorporated in the fabric material. These calibration charts (for accurate distance calculation) are added to non-stretch regions of the fabric to prevent them from distorting. For pattern projection, similar calibration charts can be used on flat projected surfaces.

In some embodiments, in additional to determining the depth information for the target object, the system captures stretch information for the fabric, where the stretch contributes to the distortion of the projected pattern from the initial pattern.

Figure 27:
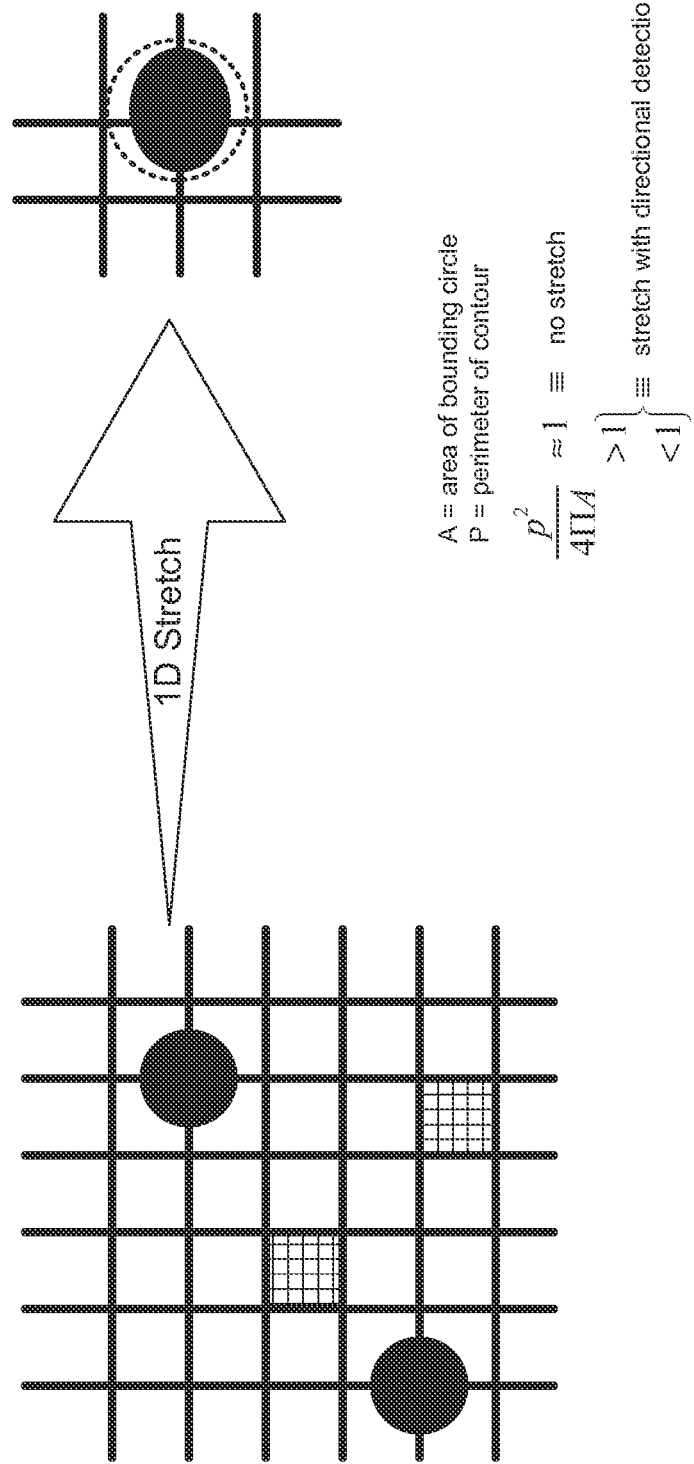
FIG. 27 illustrates an example scenario where fabric stretch results in one-dimension distortion of the projected pattern.

FIG. 27 illustrates an example scenario where fabric stretch results in one-dimension distortion of the projected pattern. In some embodiments, the initial pattern includes circles to help determine the stretch information. Circularity can be computed from second moment of contour. Initially, the area of a circle in the initial pattern can be computed as follows: $A=p^2/4\pi=(\text{Major Axis})^2 * \pi$, where p is the perimeter of the circle. The ratio $p'^2/(4\pi A)$, where p' is the perimeter of the distorted circle due to stretch can then be used to determine whether any stretch exists.

For multi-layered material that has two or more layers that exhibit different stretch properties, using patterns in different colors can help determine the amount of stretch in the different layers. For example, in some two-layered material, the first layer may stretch in a first dimension, but not in a second, while the second layer may stretch only in the second dimension, but not the first. Absence of stretch, the second layer is not visible at all. When the combined material is stretched, "reveals" are created, which indicate the direction and extent of the overall stretch. Such reveals would be reflected in the distortion of the projected pattern from the initial pattern. They can be measured for different combination of types of material through experiments, and the stretch properties of different types of material can be tabulated in advance to eliminate the effect of stretch in distortion from the computation of depth information.

Figure 28:
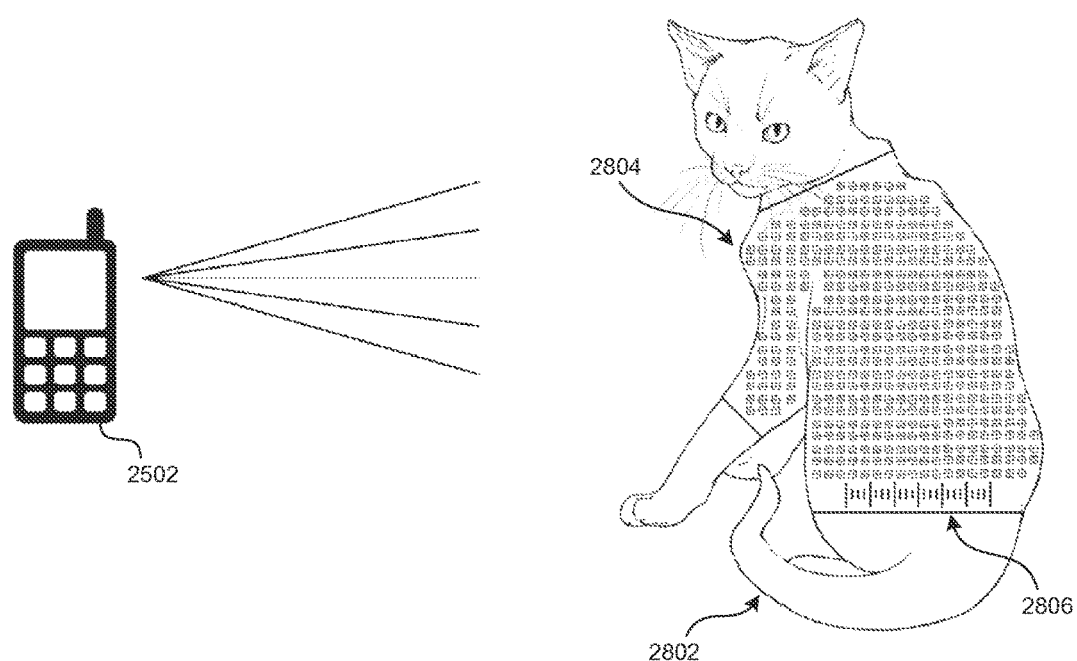
FIG. 28 illustrates an example setup of the shape measurement system that is similar to the one shown in FIG. 25.

FIG. 28 illustrates an example setup of the shape measurement system that is similar to the one shown in FIG. 25. In this example, the target object 2802 is not a human body but an animal body. This illustrates that there is not much limitation on what the target object can be. It can be inanimate, such as a rock, and it can also be simply a collection of surfaces, such as the snow on the mountain top. Also in this example, the outfit includes not only an initial pattern 2804 but also a calibration chart 2806. Information obtained from the use of the calibration chart 2806 can facilitate the analysis of the distorted pattern.

Figure 29:
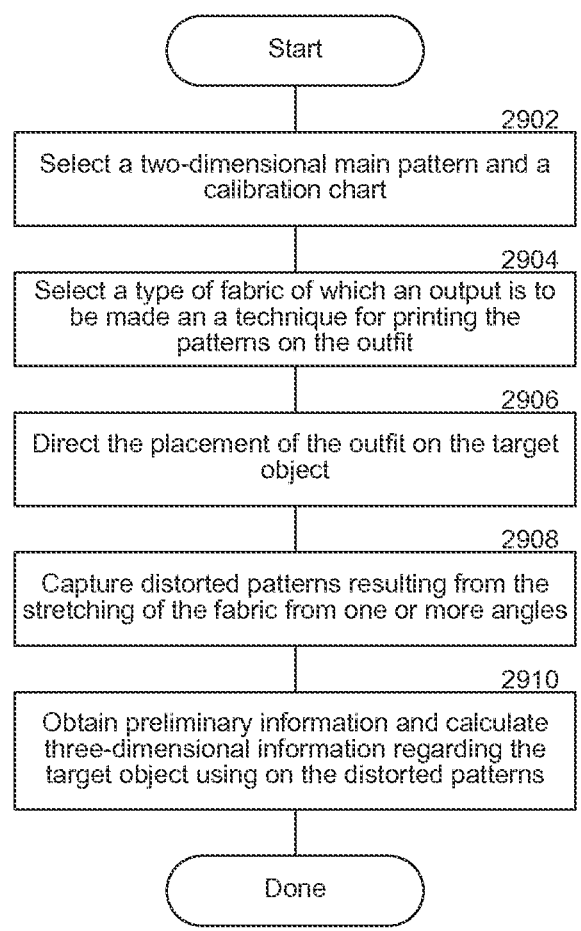
FIG. 29 illustrates another example process performed by the shape measurement system of projecting a two-dimensional pattern on a three-dimensional target object and analyzing the projected pattern in two dimensions to obtain three-dimensional information regarding the target object.

FIG. 29 illustrates another example process performed by the shape measurement system of projecting a two-dimensional pattern on a three-dimensional target object and analyzing the projected pattern in two dimensions to obtain three-dimensional information regarding the target object. In step 2902, the system selects a two-dimensional initial pattern, as discussed above, and a calibration chart. The system could also select multiple patterns to be printed on different areas of the outfit. The calibration chart is typically simple, large, and easy to detect and measure. In step 2904, the system selects a type of fabric of which an outfit is to be made and determines how to print the initial pattern and the calibration chart on the outfit. In other examples, the calibration chart can be implemented as a standalone device. The fabric should stretch to track the object in the outfit, and the printed patterns should stretch evenly as a result, and the printing should ensure that a printed pattern stretches evenly as the fabric stretches.

In step 2906, the system directs the placement of the outfit on the target object. For example, when the target object is a person's upper body, and the outfit is a top, the person is instructed to wear the top and eliminate creases, stains, or anything else that may obscure the printed patterns from the top. As the outfit is worn, the fabric stretches, and the initial pattern and calibration chart also stretch, resulting in distorted patterns.

Figure 30:
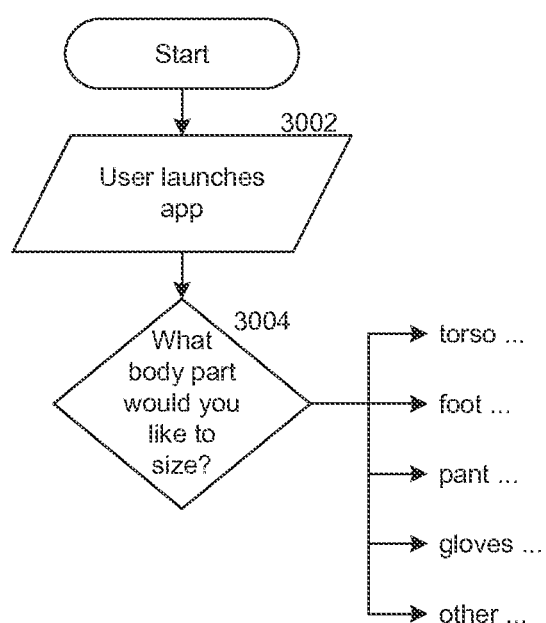
FIG. 30 illustrates an example process of guiding a user through a fitting and sizing process.

FIG. 30 illustrates an example process of guiding a user through a fitting and sizing process. In step 3002, the system is launched by the user. In step 3004, the system starts guiding the user through the "fitting" process. In step 3004, the system starts by asking which part of the user's body should be measured. Almost every part of the human body can be measured, including the torso, the foot, the gloves, and the thighs.

Figure 31:
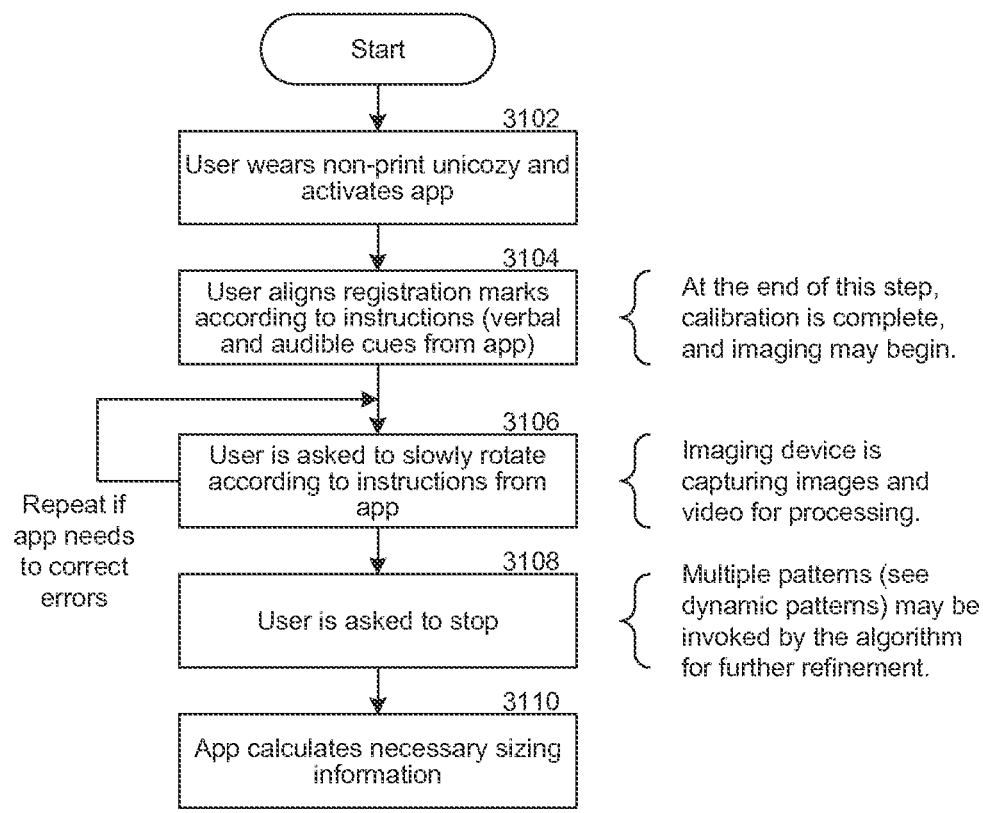
FIG. 31 illustrates another example process of guiding a user through a fitting and sizing process. In step 3102, the system continues guiding the user through the fitting process.

FIG. 31 illustrates another example process of guiding a user through a fitting and sizing process. In step 3102, the system continues guiding the user through the fitting process. In step 3102, the system instructs the user to wear the outfit. IN step 3104, the system instructs the user to place the calibration charts in certain no-stretch locations. After performing calibration using the calibration charts, in steps 3106 and 3108, the system instructs the user to slowly rotate or otherwise move so that appropriate images can be captured. In step 3110, the system extracts and examines the projected patterns and ultimately, determines the appropriate sizing information, and presents the sizing information to the user.

Referring back to FIG. 29, in step 2908, the system captures the distorted patterns. The target object can also be instructed to make movements to enable different surfaces of the target object to be visible, and the distorted patterns on all these surfaces can be captured. In step 2910, the system examines the distorted pattern corresponding to the calibration chart, obtains information useful for deriving three-dimensional information regarding the target object, including the distance to the camera, and uses the obtained information to derive three-dimensional information from the distorted pattern corresponding to the initial pattern.

Figure 32:
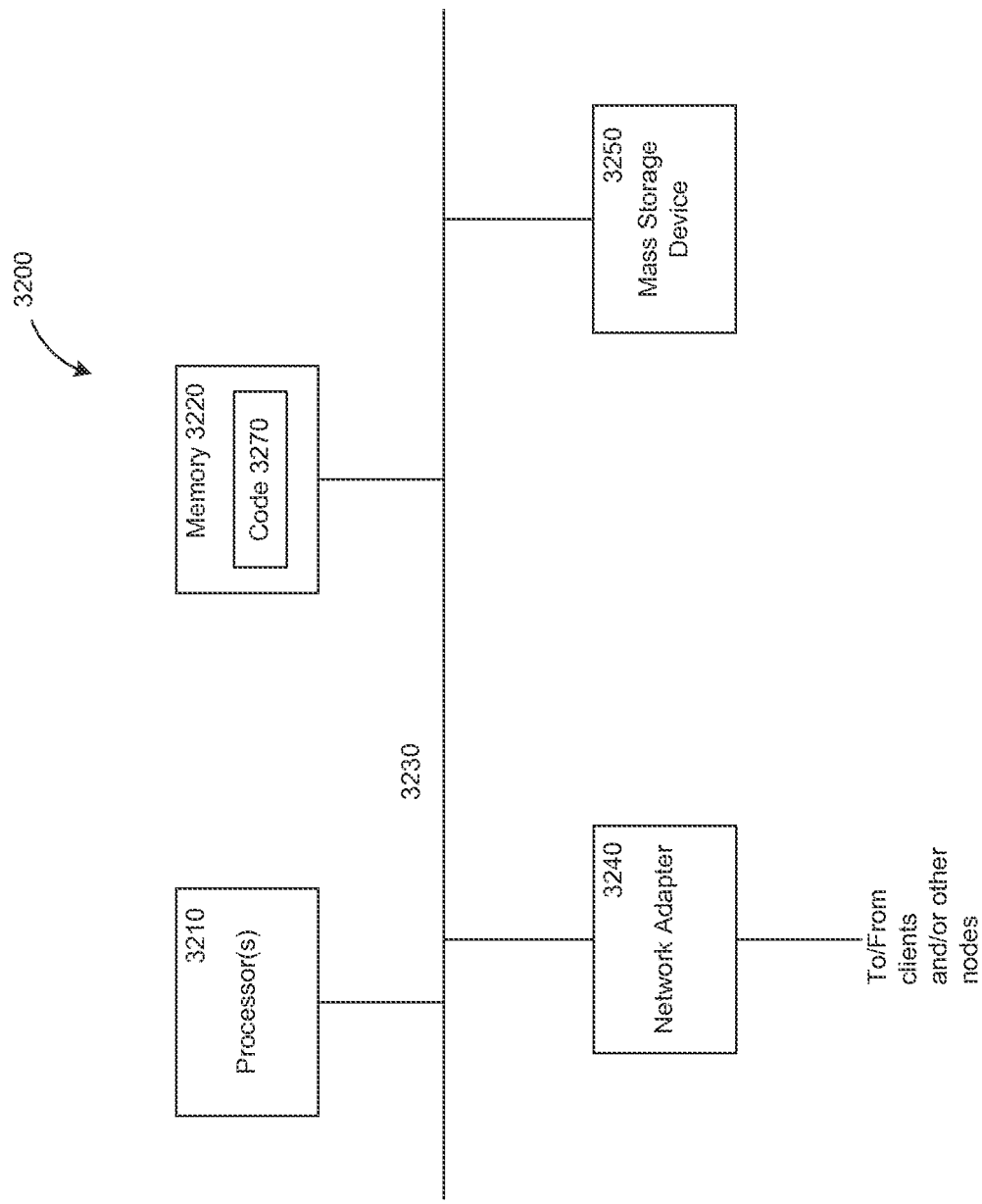
FIG. 32 contains a high-level block diagram showing an example architecture of a computer 3200, which may represent any electronic device, such as a mobile device or a server, including any node within a cloud service as described herein, and which may implement the operations described above.

FIG. 32 contains a high-level block diagram showing an example architecture of a computer 3200, which may represent any electronic device, such as a mobile device or a server, including any node within a cloud service as described herein, and which may implement the operations described above. The computer 300 includes one or more processors 3210 and memory 3220 coupled to an interconnect 3230. The interconnect 3230 shown in FIG. 32 is an abstraction that represents any one or more separate physical buses, point to point connections, or both connected by appropriate bridges, adapters, or controllers. The interconnect 3230, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The processor(s) 3210 is/are the central processing unit (CPU) of the computer 3200 and, thus, control the overall operation of the computer 3200. In certain embodiments, the processor(s) 3210 accomplish this by executing software or firmware stored in memory 3220. The processor(s) 3210 may be, or may include, one or more programmable general-purpose or special-purpose microprocessors, digital signal processors (DSPs), programmable controllers, application specific integrated circuits (ASICs), programmable logic devices (PLDs), field-programmable gate arrays (FPGAs), trusted platform modules (TPMs), or a combination of such or similar devices.

The memory 3220 is or includes the main memory of the computer 3200. The memory 3220 represents any form of random access memory (RAM), read-only memory (ROM), flash memory, or the like, or a combination of such devices. In use, the memory 3220 may contain code 3270 containing instructions according to the techniques disclosed herein.

Also connected to the processor(s) 3210 through the interconnect 3230 are a network adapter 3240 and a mass storage device 3250. The network adapter 3240 provides the computer 3200 with the ability to communicate with remote devices over a network and may be, for example, an Ethernet adapter. The network adapter 3240 may also provide the computer 3200 with the ability to communicate with other computers.

The code 3270 stored in memory 3220 may be implemented as software and/or firmware to program the processor(s) 3210 to carry out actions described above. In certain embodiments, such software or firmware may be initially provided to the computer 3200 by downloading it from a remote system through the computer 3200 (e.g., via network adapter 3240).

CONCLUSION

The techniques introduced herein can be implemented by, for example, programmable circuitry (e.g., one or more microprocessors) programmed with software and/or firmware, or entirely in special-purpose hardwired circuitry, or in a combination of such forms. Software or firmware for use in implementing the techniques introduced here may be stored on a machine-readable storage medium and may be executed by one or more general-purpose or special-purpose programmable microprocessors.

In addition to the above mentioned examples, various other modifications and alterations of the invention may be made without departing from the invention. Accordingly, the above disclosure is not to be considered as limiting, and the appended claims are to be interpreted as encompassing the true spirit and the entire scope of the invention.

The various embodiments are described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

A "machine-readable storage medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible storage medium includes recordable/non-recordable media (e.g., read-only memory (ROM); random access memory (RAM); magnetic disk storage media; optical storage media; flash memory devices; etc.), etc.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatuses, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The aforementioned flowchart and diagrams illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to some embodiments", an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

We claim:

1. A method of measuring a three-dimensional (3D) target object using two-dimensional (2D) patterns, comprising:
    selecting an initial two-dimensional pattern;
    laying the initial pattern on a 3D target object for viewing from a viewpoint to obtain a 2D transformed pattern;
    computing first depth information regarding the target object based on the transformed pattern;
    identifying a region of the target object that is hidden from the viewpoint or has a complexity above a predetermined threshold, based on the transformed pattern and first depth information;
    computing second depth information different from the first depth information regarding the region of the target object; and
    deriving a 3D measurement of the target object by combining the first depth information and the second depth information and storing the derived 3D measurement in a computer memory.

2. The method of claim 1,
    wherein the initial pattern is implemented by a standalone molding,
    the laying comprising:
    selecting a light source; and
    positioning the light source, the molding, and the target object such that light illuminated from the light source shines through the molding before forming the transformed pattern on a surface of the target object.

3. The method of claim 1,
    wherein the initial pattern is printed on an outfit made of a fabric that stretches and conforms to track a surface of the target object in the outfit, the laying comprising:
    placing the target object in the outfit so that as the fabric stretches and conforms, the initial pattern stretches into the transformed pattern.

4. The method of claim 3, further comprising:
    selecting a 2D calibration pattern;
    laying the calibration pattern on a flat portion of surface of the target object for view from the viewpoint to obtain a 2D stretch pattern; and
    computing a stretch of the stretch pattern from the calibration pattern,
    wherein the first depth information is computed based on the stretch.

5. The method of claim 3, further comprising
    wherein the laying includes obtaining multiple 2D transformed patterns corresponding to the target object at multiple positions over a period of time,
    wherein computing first depth information, identifying a region of the target object, and computing second depth information is performed for each of the multiple transformed patterns, and
    wherein the first and second depth information is used to track a movement of the target object.

6. The method of claim 1,
    wherein computing first depth information comprises:
    selecting a first portion of the initial pattern;
    determining a second portion of the transformed pattern corresponding to the first portion; and
    calculating specific depth information for a region of the target object corresponding to the second portion based on an area of the first portion, an area of the second portion, a length or diameter of the first portion, a curvature of the second portion, or a centroid of the second portion.

7. The method of claim 6, further comprising
    capturing a portion of the first transformed pattern into an image with a camera, wherein computing first depth information includes extracting the transformed pattern from the image, and
    wherein calculating specific depth information is further based on the distance between the target object to a lens of the camera.

8. The method of claim 1,
    wherein the identifying comprises:
    selecting a first portion of the initial pattern;
    determining a second portion of the transformed pattern that corresponds to the first portion;
    computing a similarity score for the first portion and the second portion; and
    when the similar score is below a predetermined threshold,
    determining whether the second portion indicates a depth discontinuity in the target object based on the first depth information.

9. The method of claim 8,
wherein the similar score is computed based on an area of the first portion and an area of the second portion.

10. The method of claim 8, further comprising,
when the second portion indicates a depth discontinuity, certifying a presence of a hidden region near the region of the target object corresponding to the second portion,
wherein computing the second depth information includes assigning specific depth information that corrects the depth discontinuity to the hidden region.

11. The method of claim 1,
when the second portion indicates no depth discontinuity, identifying a region of the target object corresponding to the second portion as a high-complexity region;
selecting a 2D second initial pattern for the region different from the first initial pattern; and
laying the second initial pattern on the target object to obtain a 2D second transformed pattern,
wherein the second depth information is computed based on the second transformed pattern.

12. The method of claim 11,
wherein the second initial pattern is selected based on the transformation pattern or is laid for viewing from a second viewpoint.

13. The method of claim 1,
wherein the initial pattern is isomorphic, repeating a configuration of lines, curves, or dots, or is an isomorphic repetition of non-isomorphic patterns.

14. The method of claim 1, further comprising
creating sizing information regarding the target object with respect to a wearable piece available in multiple sizes.

15. The method of claim 1,
wherein the target object is inanimate.

* * * * *